US012773412B2

(12) United States Patent
Vaitkevicius et al.

(10) Patent No.: US 12,773,412 B2
(45) Date of Patent: Oct. 27, 2026

(54) GANAXOLONE FOR USE IN TREATMENT OF SUPER REFRACTORY STATUS EPILEPTICUS

(71) Applicant: Immedica Pharma US Inc., Radnor, PA (US)

(72) Inventors: Henrikas Vaitkevicius, Radnor, PA (US); Maciej Gasior, Radnor, PA (US); Joseph Hulihan, Radnor, PA (US)

(73) Assignee: Immedica Pharma US Inc., Radnor, PA (US)

( * ) Notice: Subject to any disclaimer, the term of this patent is extended or adjusted under 35 U.S.C. 154(b) by 627 days.

(21) Appl. No.: 18/321,374

(22) Filed: May 22, 2023

(65) Prior Publication Data

US 2023/0364109 A1 Nov. 16, 2023

Related U.S. Application Data

(63) Continuation of application No. PCT/US2021/060459, filed on Nov. 23, 2021.

(60) Provisional application No. 63/117,037, filed on Nov. 23, 2020.

(51) Int. Cl.
*A61K 31/573* (2006.01)
*A61K 9/00* (2006.01)
*A61P 25/08* (2006.01)

(52) U.S. Cl.
CPC .......... *A61K 31/573* (2013.01); *A61K 9/0019* (2013.01); *A61P 25/08* (2018.01)

(58) Field of Classification Search
CPC ...................................................... A61K 31/57
See application file for complete search history.

(56) References Cited

U.S. PATENT DOCUMENTS

| | | | | |
|---|---|---|---|---|
| 8,022,054 | B2 | 9/2011 | Shaw et al. | |
| 8,318,714 | B2 | 11/2012 | Shaw et al. | |
| 8,362,286 | B2 | 1/2013 | Shaw et al. | |
| 8,367,651 | B2 | 2/2013 | Shaw et al. | |
| 8,618,087 | B2 | 12/2013 | Shaw et al. | |
| 9,029,355 | B2 | 5/2015 | Shaw et al. | |
| 9,056,116 | B2 | 6/2015 | Shaw et al. | |
| 10,603,308 | B2 | 3/2020 | During | |
| 11,110,100 | B2 * | 9/2021 | Czekai | A61K 31/57 |
| 11,395,817 | B2 | 7/2022 | During | |
| 11,679,117 | B2 * | 6/2023 | Czekai | A61K 31/57 514/182 |
| 11,679,167 | B2 * | 6/2023 | Coroneo | A61K 9/0048 424/9.6 |
| 12,246,026 | B2 * | 3/2025 | Czekai | A61K 31/57 |
| 2007/0141161 | A1 | 6/2007 | Shaw et al. | |
| 2007/0148252 | A1 | 6/2007 | Shaw et al. | |
| 2009/0004262 | A1 | 1/2009 | Shaw et al. | |
| 2011/0236487 | A1 | 9/2011 | Shaw et al. | |
| 2012/0052098 | A1 | 3/2012 | Shaw et al. | |
| 2012/0316146 | A1 | 12/2012 | Goodchild et al. | |
| 2014/0057885 | A1 * | 2/2014 | Reddy | A61K 31/57 514/182 |
| 2014/0249120 | A1 | 9/2014 | Covey et al. | |
| 2015/0018327 | A1 | 1/2015 | Reddy | |
| 2015/0313915 | A1 | 11/2015 | Rogawski et al. | |
| 2016/0228454 | A1 | 8/2016 | Zhang et al. | |
| 2017/0285512 | A1 | 10/2017 | Okubo et al. | |
| 2018/0071315 | A1 | 3/2018 | Cashman et al. | |

FOREIGN PATENT DOCUMENTS

| | | | | |
|---|---|---|---|---|
| CA | 2541811 A1 | 4/2005 | | |
| CA | 2892811 A1 | 6/2014 | | |
| CA | 2960611 A1 | 3/2016 | | |
| WO | WO-2007062266 A2 * | 5/2007 | | A61P 3/00 |
| WO | 2008066899 A2 | 6/2008 | | |
| WO | 2011019821 A1 | 2/2011 | | |
| WO | 2011088503 A1 | 7/2011 | | |
| WO | 2013063279 A1 | 5/2013 | | |
| WO | 2013112605 A2 | 8/2013 | | |
| WO | 2014028398 A2 | 2/2014 | | |
| WO | 2014085668 A1 | 6/2014 | | |
| WO | 2014160441 A1 | 10/2014 | | |
| WO | 2014160480 A1 | 10/2014 | | |
| WO | 2014169831 A1 | 10/2014 | | |
| WO | 2014169832 A1 | 10/2014 | | |
| WO | 2014169833 A2 | 10/2014 | | |
| WO | 2014169836 A1 | 10/2014 | | |
| WO | 2015010054 A2 | 1/2015 | | |
| WO | 2015180679 A1 | 12/2015 | | |
| WO | 2016040322 A1 | 3/2016 | | |
| WO | WO-2016127170 A1 * | 8/2016 | | A61P 25/08 |
| WO | 2017066626 A1 | 4/2017 | | |

(Continued)

OTHER PUBLICATIONS

Kerrigan et al., "Ganaxolone for treating intractable infantile spasms: a multicenter, open-label, add-on trial," Epilepsy Research, vol. 42, pp. 133-139 (2000).
Yawno et al., "Ganaxolone: A new treatment for neonatal seizures," Frontiers in Cellular Neuroscience, vol. 11, Article 246, pp. 1-7 (2017).
International Search Report and Written Opinion in PCT/US2021/060459, dated Jan. 24, 2022.

(Continued)

*Primary Examiner* — George W Kosturko

(74) *Attorney, Agent, or Firm* — Knobbe, Martens, Olson & Bear, LLP

(57) ABSTRACT

This invention relates to methods for treating super refractory status epilepticus by rapidly weaning the subject in need thereof off an anesthetic agent prior to initiation of administering to the subject in need thereof of ganaxolone at a high infusion dose. The method provides SE suppression and continued suppression of SE.

16 Claims, 8 Drawing Sheets

(56) References Cited

FOREIGN PATENT DOCUMENTS

Figure 1:
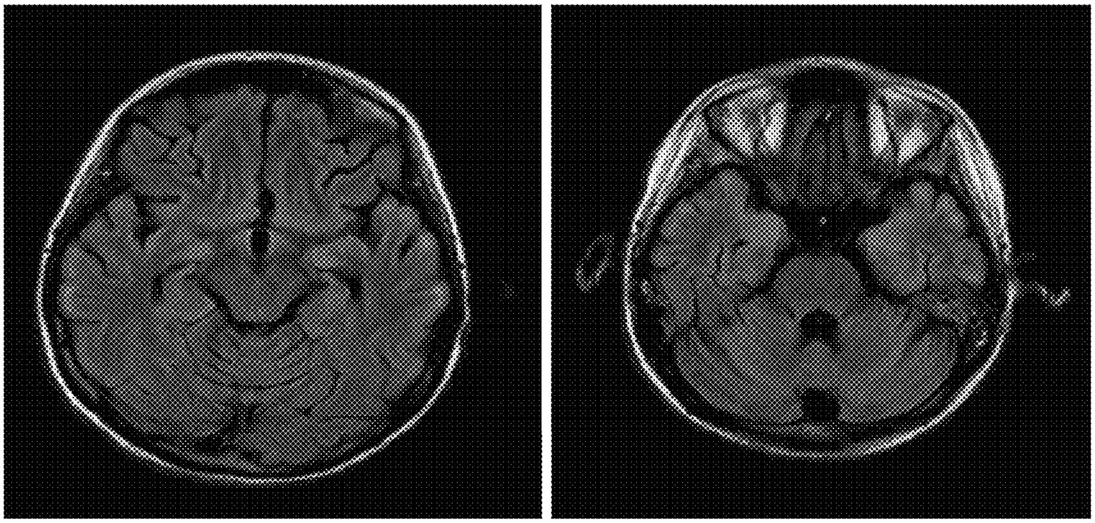

| | | | | |
|---|---|---|---|---|
| WO | 2017156103 A1 | 9/2017 | | |
| WO | 2018031748 A1 | 2/2018 | | |
| WO | WO-2018071803 A1 * | 4/2018 | .............. | A61P 25/08 |
| WO | 2018195186 A1 | 10/2018 | | |
| WO | 2019094724 A1 | 5/2019 | | |
| WO | 2021026124 A1 | 2/2021 | | |
| WO | 2021113834 A1 | 6/2021 | | |
| WO | 2022109440 A1 | 5/2022 | | |
| WO | 2022125408 A1 | 6/2022 | | |

OTHER PUBLICATIONS

Saporito et al., Intravenous Administration of Ganaxolone Attenuates Electroencephalographic Seizures in a Diazepam Resistant Model of Status Epilepticus, Neurobiology, 86 (16 supplement), published Apr. 4, 2016.

Press Release: "Marinus Pharmaceuticals Doses First Subject in Phase 1 Clinical Trial for Ganaxolone IV," Published on Jun. 22, 2016, Available at: https://ir.marinuspharma.com/news/news-details/2016/Marinus-Pharmaceuticals-Doses-First-Subject-in-Phase-1-Clinical-Trial-for-Ganaxolone-IV/default.aspx.

Press Release: "Marinus Pharmaceuticals Receives FDA Orphan Drug Designation for Ganaxolone IV to Treat Status Epilepticus," Published Apr. 15, 2016, Available at: https://ir.marinuspharma.com/news/news-details/2016/Marinus-Pharmaceuticals-Receives-FDA-Orphan-Drug-Designation-for-Ganaxolone-IV-to-Treat-Status-Epilepticus/default.aspx.

Chez, "Ganaxolone Therapy Improves Interictal EEG and Seizure Control in Lennox Gastaut Syndrome in Patients with PCDH19 and CDKL5," Annals of Neurol. 80 (suppl 20)published Oct. 26, 2016.

Saporito et al., Ganaxolone Administered Intravenously Prevents Behavioral Seizures and Promotes Survival in the Rat Lithium-Pilocarpine Model of Status Epilepticus, Neurology, 86 (16 Supplement), published Apr. 5, 2016 (available at: https://n.neurology.org/content/86/16_Supplement/111.003).

Press Release: "Marinus Announces Clinical Development Plans for Ganaxolone Intravenous Formulation," Published on Oct. 29, 2015 (available at: https://ir.marinuspharma.com/news/news-details/2015/Marinus-Announces-Clinical-Development-Plans-for-Ganaxolone-Intravenous-Formulation/default.aspx).

Press Release: "Marinus Pharmaceuticals Provides Business Update and Reports Second Quarter 2016 Financial Results," Published on Aug. 9, 2016 (available at: https://ir.marinuspharma.com/news/news-details/2016/Marinus-Pharmaceuticals-Provides-Business-Update-and-Reports-Second-Quarter-2016-Financial-Results/default.aspx).

Press Release: "Marinus Pharmaceuticals' Ganaxolone IV Demonstrates Robust Efficacy in Benzodiazepine-Resistant Models of Status Epilepticus," Published on Apr. 19, 2016, (available at: https://ir.marinuspharma.com/news/news-details/2016/Marinus-Pharmaceuticals-Ganaxolone-IV-Demonstrates-Robust-Efficacy-in-Benzodiazepine-Resistant-Model-of-Status-Epilepticus/default.aspx).

Rogawski et al.; "Neuroactive Steroids for the Treatment of Status Epilepticus"; Epilespsia, vol. 54(6); pp. 93-98 (2013).

Rosetti et al.; "Management of Refractory Status Epilepticus in Adults: Still More Questions Than Answers"; Lancet Nuerol., vol. 10; pp. 922-930 (2011).

Shorvon et al.; "The Treatment of Super-Refractory Status Epilepticus: A Critical Review of Available Therapies and a Clinical Treatment Protocol", Brain, vol. 134; pp. 2802-2818 (2011).

Reddy and Kuruba, "Experimental Models of Status Epilepticus and Neuronal Injury for Evaluation of Therapeutic Interventions," Int. J. Mol. Sci. 14:18284-318 (2013).

Seinfeld et al., "Status Epilepticus," in Additional Perspectives on Epilepsy: The Biology of a Spectrum Disorder (Cold Spring Harbor Laboratory Press, 2016, ed. Gregory L. Holmes and Jeffrey L Noebels).

Imtiyaz et al., "The Evolution of the Pilocarpine Animal Model of Status Epilepticus," Heliyon 6:e04557 (2020).

Turski, et al., "Review: Cholinergic Mechanisms and Epileptogenesis. The Seizures Induced by Pilocarpine: A Novel Experimental Model of Intractable Epilepsy," Synapse 3:154-71 (1989).

Kokate et al., "Neuroactive Steroids Protect Against Pilocarpine- and Kainic Acid-induced Limbic Seizures and Status Epilepticus in Mice," Neuropharmacology, 35(8):1049-56 (1996).

American Academy of Neurology ("AAN") 2016 Annual Meeting Scientific Abstract Listing and Meeting Information, AAN 2016 Annual Meeting, Vancouver, BC, Canada, Apr. 15-21, 2016, Available at: https://issuu.com/americanacademyofneurology/docs/16am_abs traclistingdigi_v1424.

Saporito et al., "Ganaxolone Administered Intravenously Prevents Behavioral Seizures and Promotes Survival in the Rat Lithium-Pilocarpine Model of Status Epilepticus," Poster, presented Apr. 17, 2016, at the 2016 AAN Annual Meeting.

Saporito et al., "Intravenous Administration of Ganaxolone Attenuates Electroencephalographic Seizures in a Diazepam Resistant Model of Status Epilepticus," Poster, presented Apr. 19 and Apr. 20, 2016, at the 2016 AAN Annual Meeting.

Saporito, "Ganaxolone Administered IV Blocks Experimental Status Epilepticus," "Data Blitz" Presentation, Aril 20, 2016, at the 2016 AAN Annual Meeting.

Wylie et al., Status Epilepticus. [Updated May 15, 2022]. In: StatPearls [Internet]. Treasure Island (FL): StatPearls Publishing; Jan. 2022—. Available from: https://www.ncbi.nlm.nih.gov/books/NBK430686/.

Trinka et al., "A definition and classification of status epilepticus-Report of the ILAE Task Force on Classification of Status Epilepticus." Epilepsia, 56(10):1515-1523 (2015).

Tsai et al., "Phase I Study to Determine the Pharmacokinetics, Pharmacodynamics, and Safety of IV Ganaxolone in Healthy Adults," Abstract of Poster Presented at the 6th London-Innsbruck Colloquium on Status Epilepticus and Acute Seizures Apr. 6-8, 2017, Salzburg, Austria.

2016 AAN Annual Report.

Drug Development and Review Definitions, Aug. 20, 2015, Available at: https://www.fda.gov/drugs/investigational-new-drug-ind-application/drug-development-and-review-definitions.

Press Release: "Marinus Pharmaceuticals Doses First Subject in Phase I Clinical Trial for Ganaxolone IV," Published on Jun. 22, 2016, Available at: https://ir.marinuspharma.com/news/news-details/2016/Marinus-Pharmaceuticals-Doses-First-Subject-in-Phase-1-Clinical-Trial-for-Ganaxolone-IV/default.aspx.

Carter et al., "Characterization of the Anticonvulsant Properties of Ganaxolone (CCD 1042: 3α-Hydroxy-3β-methyl-5α-pregnan-20-one), a Selective, High-Affinity, Steroid Modulator of the γ-Aminobutyric AcidA Receptor," The Journal of Pharmacology and Experimental Therapeutics, 280(3):1284-95 (1997).

Saporito et al., Intravenous Administration of Ganaxolone Attenuates Electroencephalographic Seizures in a Diazepam Resistant Model of Status Epilepticus, Neurobiology, 86 (16 supplement), Abstract, published Apr. 4, 2016.

Saporito et al., Ganaxolone Administered Intravenously Prevents Behavioral Seizures and Promotes Survival in the Rat Lithium-Pilocarpine Model of Status Epilepticus, Neurology 86 (16 Supplement), Abstract, published Apr. 4, 2016.

Chez, "Ganaxolone Therapy Improves Interictal EEG and Seizure Control in Lennox Gastaut Syndrome in Patients with PCDH19 and CDKL5," Annals of Neurol. 80 (suppl 20), S326 published Oct. 26, 2016.

* cited by examiner

GANAXOLONE FOR USE IN TREATMENT OF SUPER REFRACTORY STATUS EPILEPTICUS

The present application claims the benefit of International Application No. PCT/US2021/060459, filed on Nov. 23, 2021, which claims the benefit of U.S. Provisional Application No. 63/117,037, filed on Nov. 23, 2020, the entire contents of which are incorporated herein by reference.

1. BACKGROUND

Status epilepticus ("SE") is a life-threatening neurological emergency associated with significant morbidity and mortality (Betjemann and Lowenstein, (2015) The Lancet Neurology, 14 (6): 615-624). SE is manifested by prolonged seizure activity, typically persisting more than 5 minutes, or recurrent seizures without recovery of consciousness between seizures. Id. SE requires aggressive treatment to stop the seizure and prevent neurological damage, including neuronal death. SE becomes more difficult to control as its duration increases, and prolonged SE and refractoriness to treatment are associated with poor prognosis (Cherian & Thomas (2009), Ann. Indian. Acad. Neurol., 12 (3): 140-153). Goals of treatment are rapid seizure cessation, maintenance of seizure control, preventing progression to anesthetics and avoiding further medical complications. Id.

Super-refectory SE ("SRSE") is the most severe form of SE and is associated with long-term neurological dysfunction. SRSE occurs in 23% to 43% of patients with SE and is associated with a high mortality of up to 50% (Lionel and Hrishi, Indian J. Crit. Care Med. 20(10): 587-592 (2016)). SRSE is SE that continues or recurs despite therapy with general anesthesia using anesthetic antiepileptic drugs (midazolam, propofol, ketamine, or barbiturate) for more than 24 hours or recurrence of SE on weaning of general anesthetics. Shorvon S, Ferlisi M. Brain 2011:134-2802-2818. These patients are severely ill and will likely die without further intervention.

An SE patient is first treated with first-line therapeutic agents, typically with benzodiazepines (e.g., diazepam, lorazepam, and midazolam) (Trinka and Kälviäinen (2017), Seizure, 44:65-73; Glauser et al., (2016), Epilepsy Curr. 26 (1): 48-61). If the patient does not respond, the patient is then treated with other, second-line, anti-seizure drugs. Id. If the seizure persists after one second-line anti-epileptic drug, the patient is diagnosed as having refractory SE. After failure of second-line therapy, the patient is admitted to the ICU and placed into a medically induced coma. Id. Physicians typically use one or more anesthetic agents (e.g., thiopental, propofol, and midazolam) to induce the coma, along with antiepileptic drugs in an attempt to stop the ongoing seizure, in refractory SE patients. Id. After a period of 24 hours, an attempt is made to slowly wean the patient from the anesthetic agents to evaluate whether or not the seizure condition has resolved. Unfortunately, not all patients respond to weaning attempts, and those who do not are considered to have SRSE and must be maintained in the medically induced coma. In many instances, these patients die without further intervention. It is estimated that there are between 25,000 and 41,000 cases of SRSE in the U.S. each year.

Currently, there are no therapies specifically approved for SRSE. Typically SRSE patients are treated with anesthetics (frequently a two or more anesthetics) that are administered to place and maintain the SRSE patient in burst suppression with no ictal activity. Unfortunately, the brain adjusts to this type of treatment over a period of time and when anesthetics are reduced or withdrawn, the patient frequently shows hyperactive brain activity including recurrence of seizure. Consequently, SRSE patients are typically weaned off anesthetics very slowly and typically by reducing anesthetics by no more than about 20% per day. Moreover, some recent attempts to develop new treatments have failed. For example, brexanolone (SAGE-547), a formulation of endogenous allopregnanolone, failed to show efficacy over placebo in a randomized, double-blind, placebo-controlled trial for the treatment of SRSE. (Sage Pharmaceuticals press release Sep. 12, 2017, www.businesswire.com/news/home/20170912005509/en/Sage-Therapeutics-Reports-Top-Line-Results-Phase-3). Accordingly, there is a significant unmet need for effective therapies for treating SRSE.

2. SUMMARY

The disclosure relates to methods of treating SRSE. As noted above, SRSE is an extremely challenging and complicated condition to treat and general anesthesia remains the basis of medical therapy. Developing new treatments for SRSE has been significantly challenging and largely unsuccessful. For example, brexanolone (i.e., allopregnanolone) failed to show efficacy over placebo in a double blind, placebo-controlled Phase 3 trial in patients with super refractory SE. As a result, many of these patients die.

As described and exemplified herein, the inventors believe that ganaxolone holds promise as an effective therapy for SRSE. The inventors previously discovered that administering ganaxolone as an intravenous bolus plus continuous infusion to maintain plasma concentration of ganaxolone at 500 ng/ml or higher for a target concentration period of at least about 8 hours resulted in rapid and continued suppression of SE. However, as discussed above, SRSE patients are an extremely ill subset of patients in which SE continues or recurs despite therapy with anesthetic agents (e.g., midazolam, propofol, ketamine, or barbiturate). Furthermore, the brain adjusts to these anesthetic agents over a period of time and the patient frequently shows hyperactive brain activity, including recurrence of seizure, when the anesthetics are reduced or withdrawn. When this occurs, the patient is typically then re-administered anesthetic agents at doses to cause burst suppression and to induce coma. As such, patients are typically weaned off anesthetics very slowly and typically by reducing anesthetics by no more than about 20% per day.

The inventors surprisingly discovered that SRSE patients can be more effectively treated using ganaxolone as a therapeutic bridge, and if indicated as chronic therapy. Without being bound by theory, the inventors believe that rapidly weaning the subject off the anesthetic agent and briefly allowing ictal activity (e.g., seizure) to return and then administering ganaxolone to manage ictal activity while continuing to actively withdraw anesthesia, maximizes ganaxolone exposure without the presence of anesthetics and hence increases the chance of successful wean from anesthetic agents, perhaps due to reducing occupancy of $GABA_A$ receptors, the site of action for both ganaxolone and many anesthetic agents. Ganaxolone can then be used to manage ictal activity and the patient can be weaned off ganaxolone without causing the hyperresponsiveness that is caused by withdrawing anesthetics. This approach provides many therapeutic advantages. Notably, the patient can regain consciousness and be extubated. Also, less ganaxolone is typically required to manage ictal activity and ganaxolone can be tapered (e.g., the patient can be weaned off ganaxolone) over a brief period of about 12 hours or less.

In some practices of the method, anesthesia is rapidly reduced (e.g. reduced at least 20% or more per day) until ictal activity that is not considered to be tolerable is observed, and then ganaxolone is administered, typically by infusion at high dose (such as a dose that achieves and maintains a ganaxolone serum concentration of at least about 800 ng/ml or 900 ng/ml) for at least about 2.5 hours and up to about 5 days or longer (e.g., up to about two weeks) to suppress unacceptable ictal activity (e.g., SE and/or seizure) and permit withdrawal of anesthetic. For example, ganaxolone can be administered to the subject for at least about 24 hours to about 5 days or longer, about 36 hours to about 5 days or longer, about 48 hours to about 5 days or longer, about 72 hours to about 5 days or longer, about 96 hours to about 5 days or longer, about 4 days or more, about 5 days or more (e.g., 6 days, 7 days, 8 days, 9 days, 10 days). Preferably, ganaxolone is administered for 36 hours up to about 5 days.

If desired the amount of ganaxolone that is administered can be reduced after the initial about 2.5 hours, but typically will be sufficient to suppress SRSE break through (e.g., an amount that achieves and maintains a ganaxolone serum concentration of at least about 400 ng/mL, at least about 500 ng/mL, at least about 600 ng/ml or higher). For example, the ganaxolone can be administered as a bolus plus continuous intravenous infusion. The anesthetic agent is rapidly weaned by reducing the anesthetic agent by about 20% and preferably up to about 30% at about 8 hour intervals. The inventors determined that ictal activity (e.g. seizure activity) is typically considered unacceptable when the subject has an EEG ictal burden of about 20% for at least about 30 minutes as defined by the modified Salzburg criteria. At this point, treatment with ganaxolone is typically initiated.

This approach is contrary to conventional treatment of SRSE that slowly weans patients off anesthetic agents. If seizure re-lapse or abnormal EEG activity is observed, the patient is then re-administered anesthetic agents at doses to cause burst suppression and to induce coma. And, in these cases the patient often sustains neurological damage or dies from systemic complications.

Accordingly, this disclosure relates to a method for effectively treating SRSE that provides rapid suppression of SRSE while allowing for recovery of hyperexcitable state, sustained efficacy (i.e., prevents SE-relapse and provides for continued suppression of SE), and improved safety.

The methods disclosed herein comprise rapidly weaning a subject in need thereof off an anesthetic agent and allowing ictal activity (e.g. seizure) to return prior to initiation of treatment with ganaxolone. The subject typically has an EEG pattern of burst suppression prior to and/or during weaning off an anesthetic agent. The anesthetic agent can be rapidly weaned by reducing the dose by at least about 20% and up to around 30% of the anesthetic agent at about 8 hour intervals. Unacceptable ictal activity is typically considered to be an EEG ictal burden of about 20% for at least 30 minutes. At this point, treatment with an effective amount of a neurosteroid, preferably ganaxolone, is started, for example as an intravenous bolus plus continuous intravenous infusion.

The intravenous bolus is administered in an amount to suppress unacceptable ictal activity (e.g. SE). Suppression of SE reduces seizure burden. Typically, a ganaxolone plasma concentration of about 800 ng/ml to about 1200 ng/ml is sufficient to suppress unacceptable ictal activity (e.g., SE). For example, to rapidly achieve a ganaxolone plasma concentration level of 800 ng/ml to about 1200 ng/ml, an intravenous bolus infusion of about 5 mg to about 40 mg of ganaxolone can be administered to the subject at the initiation of the loading infusion. Preferably, about 30 mg of ganaxolone is infused into the subject at the initiation of the intravenous bolus or during the intravenous bolus. In subjects' that weigh less than 40 kg, an intravenous bolus infusion of about 0.07 mg/kg to about 0.57 mg/kg of ganaxolone can be administered to the subject at the initiation of the loading infusion. Preferably, about 0.43 mg/kg is administered the subject that weighs less than 40 kg at the initiation of the intravenous bolus or during the intravenous bolus. Preferably, about 0.75 mg/kg is administered the subject that weighs less than 40 kg at the initiation of the intravenous bolus or during the intravenous bolus. The intravenous bolus can be administered (i.e., infused) to the subject for about 1 minute to about 5 minutes.

A continuous intravenous infusion of ganaxolone can be administered for a target concentration period in an amount sufficient for continued suppression of SRSE. The continuous intravenous infusion of ganaxolone is initiated periprocedural with the intravenous bolus. The continuous intravenous infusion is generally administered concurrently with the administration of the intravenous bolus. In some cases, the continuous intravenous infusion can be initiated before or after the intravenous bolus. It is preferred that the continuous intravenous infusion maintains a high dose of ganaxolone.

Continued suppression of SRSE is achieved when the continuous intravenous infusion maintains a plasma concentration of ganaxolone of about 800 ng/ml or higher throughout a target concentration period of at least about 2.5 hours and up to 5 days. For example, ganaxolone can be administered to the subject for at least about 24 hours to about 5 days, about 36 hours to about 5 days, about 48 hours to about 5 days, about 72 hours to about 5 days, about 96 hours to about 5 days, about 4 days or more, about 5 days or more (e.g., 6 days, 7 days, 8 days, 9 days, 10 days). Preferably, ganaxolone is administered for 36 hours up to about 5 days. Although, the amount administered can be reduced to achieve and maintain a lower ganaxolone plasma concentration but should be maintained at a level to prevent break through seizure (e.g., to maintain a serum concentration of at least about 500 ng/mL, at least about 600 ng/mL, at least about 700 ng/ml or higher).

The continuous intravenous infusion is administered throughout the treatment period, which includes the target concentration period, during which the subject's plasma concentration of ganaxolone is maintained at or above a target concentration, such as about 800 ng/ml, about 850 ng/ml, about 900 ng/ml, about 1000 ng/ml, or about 1200 ng/ml. Preferably, the target concentration is a plasma concentration of ganaxolone of 800 ng/ml or 900 ng/ml. Typically, a ganaxolone plasma concentration about 800 ng/ml, about 850 ng/ml, about 900 ng/ml, about 1000 ng/ml, or about 1200 ng/ml for a target concentration period is sufficient for SRSE suppression. Following the target concentration period, a ganaxolone plasma concentration of about 425 ng/ml, at least about 450 ng/ml, or at least about 475 ng/ml or is preferably at least about 500 ng/ml can be sufficient to maintain continued SE suppression. Generally, it is desired that the ganaxolone plasma concentration is not higher than about 1000 ng/ml. This is because a ganaxolone plasma concentration of higher than 1000 ng/ml can induce anesthesia, which is not a desired effect of the treatment. However, the prescribing physician will appreciate that some severely ill patients will benefit from a ganaxolone plasma concentration of greater than 1000 ng/ml.

The target concentration period is typically at least about 2 hours to about 5 hours. Although, it is possible that the target concentration can be longer, for example up to 5 days and in some cases longer. Typically, the amount of ganaxolone administered to the subject per hour by continuous intravenous infusion during the target concentration period can be increased or decreased to maintain continued suppression of SE, but is sufficient to maintain a ganaxolone plasma concentration of at least about 800 ng/ml.

The amount of ganaxolone administered to the subject per hour by continuous intravenous infusion can be decreased over a period of about 24 hours from the initiation of the continuous intravenous infusion. The amount of ganaxolone administered to the subject per hour by continuous intravenous infusion can be decreased about 2 hours and/or about 10 hours to about 14 hours after the initiation of the continuous intravenous infusion. The amount of ganaxolone administered to the subject per hour by continuous intravenous infusion can be decreased about 2 hours after the initiation of the continuous intravenous infusion and then about 10 hours to about 14 hours after the initiation of the continuous intravenous infusion.

The amount of ganaxolone administered to the subject per hour by continuous intravenous infusion can be decreased by about 50%, relative to the amount administered per hour at the initiation of the continuous intravenous infusion, about 2 hours after the initiation of the continuous intravenous infusion. The amount of ganaxolone administered to the subject per hour by continuous intravenous infusion can be decreased by about 55%-75%, relative to the amount administered per hour at the initiation of the continuous intravenous infusion, about 10 hours to about 14 hours after the initiation of the continuous intravenous infusion. The amount of ganaxolone administered to the subject per hour by continuous intravenous infusion can be decreased by about 50%, relative to the amount administered per hour at the initiation of the continuous intravenous infusion, about 2 hours after the initiation of the continuous infusion, and then by about 55%-75%, relative to the amount administered per hour at the initiation of the continuous intravenous infusion, about 10 hours to about 14 hours after the initiation of the continuous infusion.

The amount of ganaxolone administered to the subject per hour by continuous intravenous infusion can be decreased by about 50%, relative to the rate given during the target concentration period at 2 to 12 hours after initiation of the infusion. After another 12 to 24 hours after the initiation of the continuous intravenous, the continuous intravenous infusion can again be decreased by half, or 75% of the target concentration period infusion rate.

About 20 mg of ganaxolone per hour to about 80 mg of ganaxolone per hour can infused into the subject during the continuous infusion treatment period. In general, about 80 mg of ganaxolone per hour can be infused into the subject at the initiation of the continuous intravenous infusion. After about 2 hours, amount of ganaxolone can then be decreased to about 40 mg of ganaxolone per hour then to about 35 mg of ganaxolone per hour during the treatment period. In some instances, about 80 mg of ganaxolone can be administered to the subject by the continuous intravenous infusion from initiation and for about 2 hours thereafter, then about 40 mg of ganaxolone per hour can be administered to the subject by continuous intravenous infusion starting about 2 hours after initiation and for about 2 hours to about 10 hours thereafter, then about 35 mg of ganaxolone per hour can be administered to the subject by continuous intravenous infusion starting about 12 hours after initiation and for about 12 hours to about 24 hours thereafter.

The amount of ganaxolone administered to the subject per by continuous intravenous infusion can be increased, decreased, not change after about 24 hours from the initiation of the intravenous infusion. The amount of ganaxolone administered be hour by continuous intravenous infusion is typically decreased by about 5% to about 15%, relative to the amount administered per hour starting after 24 hours after initiation of the continuous intravenous infusion for the remaining treatment period. For example, the amount of ganaxolone infused into the subject by continuous intravenous infusion can be decreased to about 30 mg of ganaxolone per hour, starting at about 24 hours after the initiation and for the remaining treatment period (e.g., up to 96 hours, up to 120 hours, up to 144 hours, up to 168 hours or longer). For example. The amount of ganaxolone infused into the subject by continuous intravenous infusion can be decreased to about 30 mg of ganaxolone per hour, starting at about 24 hours after the initiation and for the remaining treatment period for about 72 hours.

The amount of ganaxolone administered per hour by continuous intravenous infusion can be increased by up to by about 45%, relative to the amount administered per hour starting after about 24 hours after initiation of the continuous intravenous infusion. For instance, the amount of ganaxolone infused into the subject by continuous intravenous infusion can be increased up to about 40 mg of ganaxolone per hour, but preferably does not exceed 40 mg, starting about 24 hours after the initiation and for up to about 96 hours or longer thereafter. The amount of ganaxolone can be increased for a period of up to 96 hours or longer.

The amount of ganaxolone administered per hour by continuous intravenous infusion can be remain unchanged relative to the amount administered at about 24 hours after initiation of the continuous intravenous infusion and for the remaining treatment period.

In general, the maximum daily dose of ganaxolone administered is about 1050 mg.

The treatment period of the continuous intravenous infusion can be for a period of about 36 hours, about 48 hours, about 72 hours, about 96 hours, about 120 hours or longer after the initiation of the intravenous infusion. Preferably, the treatment period is for a period of up to about 96 hours after the initiation of the continuous intravenous infusion.

The continuous intravenous infusion is typically followed by a tapering period. The taper period generally starts at about 36 hours up to about 168 hours (7 days) or longer from the initiation of the continuous intravenous infusion. During the taper period the continuous intravenous infusion of ganaxolone is systematically decreased, typically by reducing the amount of ganaxolone that is administered to the subject by about one third every four hours until the subject no longer requires ganaxolone.

The continuous intravenous infusion can be supplement with one or more additional intravenous bolus doses of ganaxolone. The additional intravenous bolus can be administered to maintain a ganaxolone plasma concentration of at least about 500 ng/ml, preferably at least about 800 ng/ml.

Oral ganaxolone can be used after the taper period to maintain a ganaxolone serum concentration at a level for continued SE suppression, for example at least about 50 ng/ml to about 500 ng/ml. Oral ganaxolone can also be used at the initiation of or during the taper period to maintain a ganaxolone serum concentration at a level for continued SE suppression, for example at least about 50 ng/ml to about 500 ng/ml.

3. BRIEF DESCRIPTION OF DRAWINGS

FIG. 1 shows an MRI image during prolonged status epilepticus in the subject described in Example 2. The MRI image shows marked progression of diffuse global parenchymal atrophy since 5 months prior, predominantly affecting the white matter. Increasing T2 FLAIR hyperintensity in the subcortical and juxta cortical white matter. Signal abnormality is most pronounced in the U fibers of the parietal and temporal lobes. MRI, magnetic resonance imaging; T2 FLAIR, T2-weighted fluid-attenuated inversion recovery; PT, patient.

Figure 2:
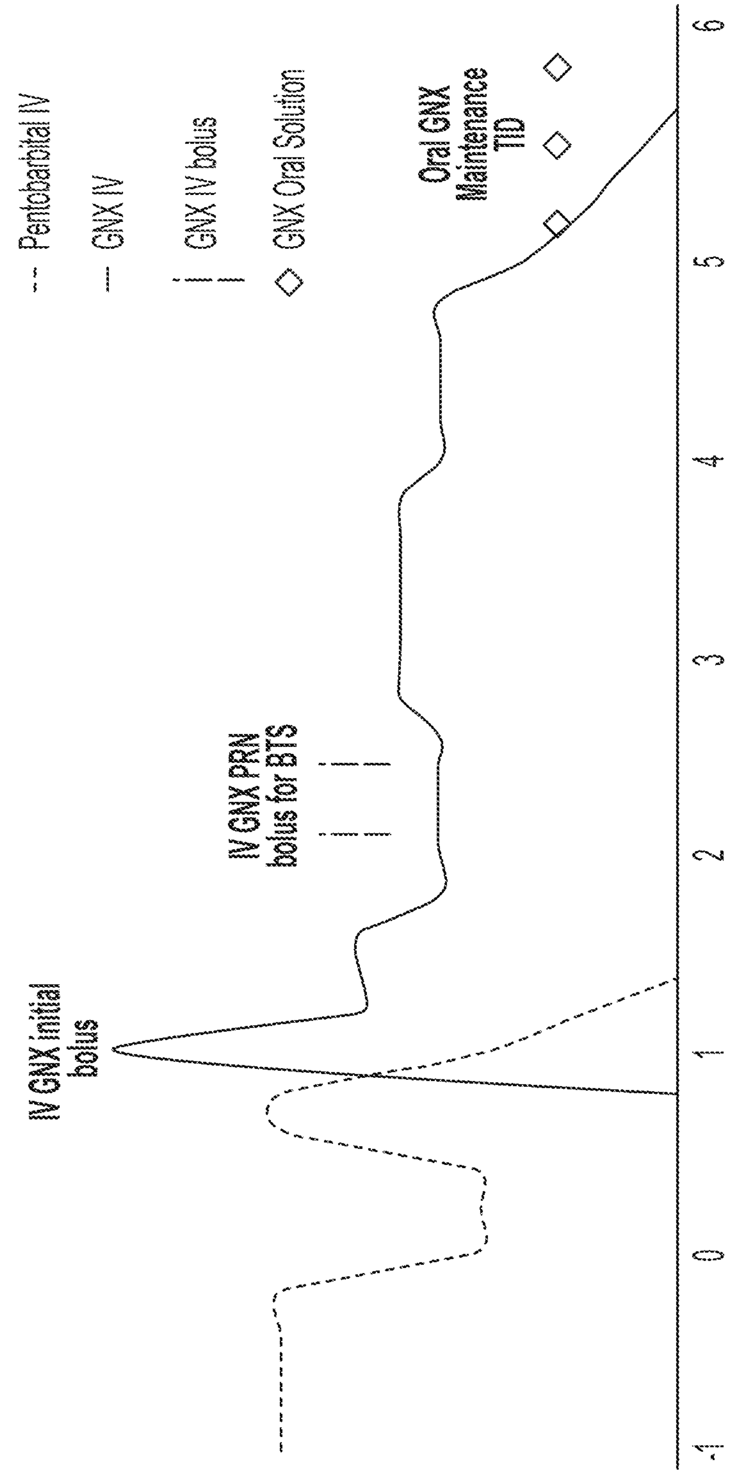

FIG. 2 shows a graph of the ganaxolone dosing regimen for the patient described in Example 2.

Figure 3A:
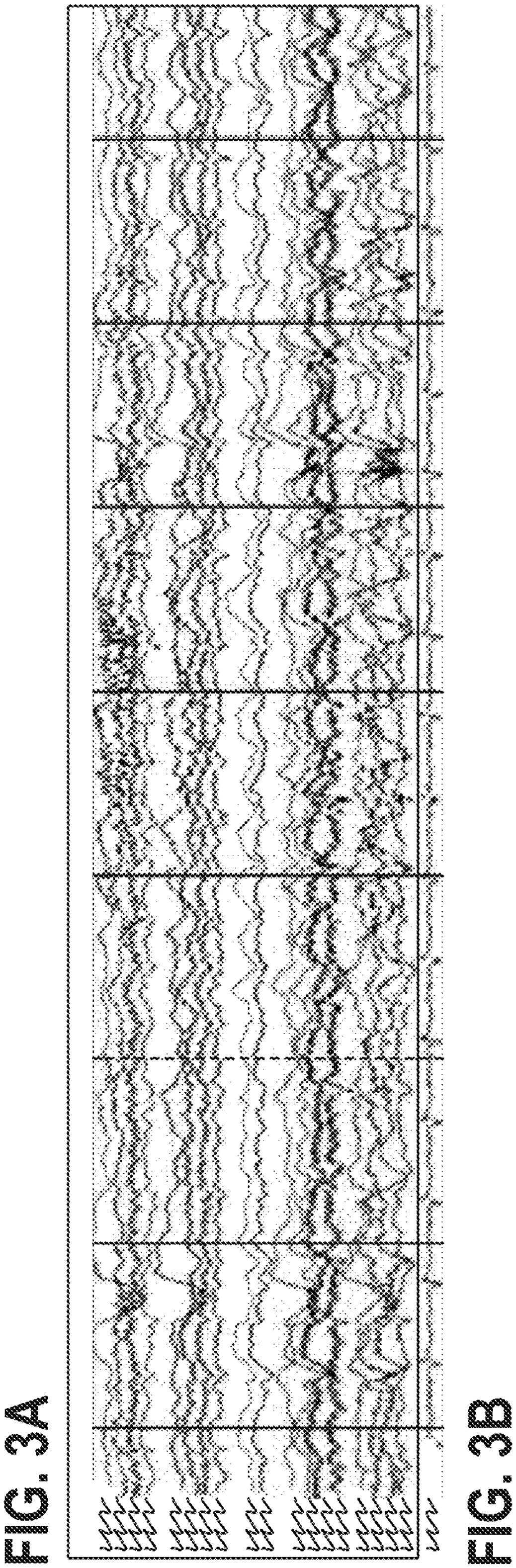
Figure 3B:
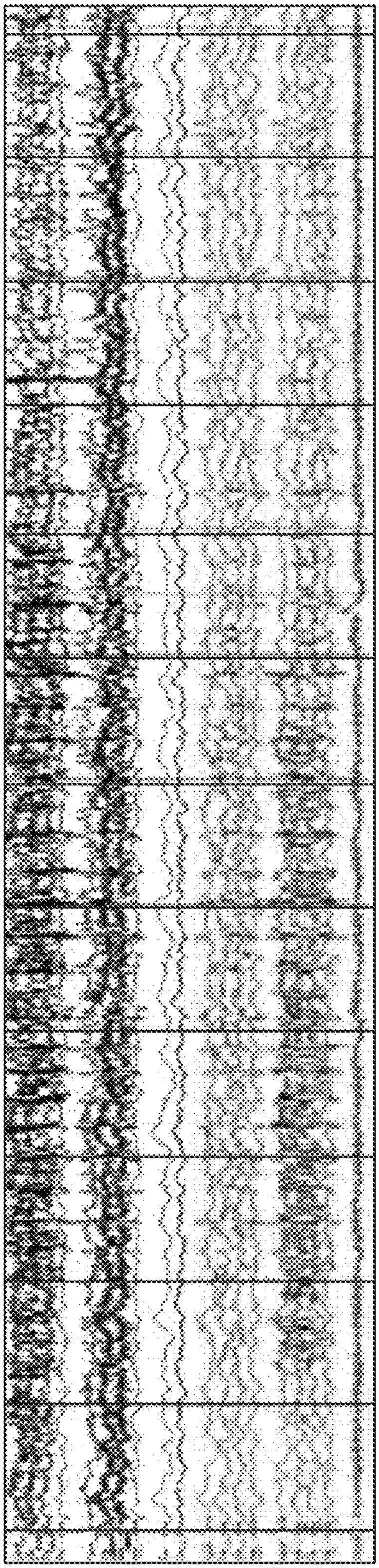
Figure 3C:
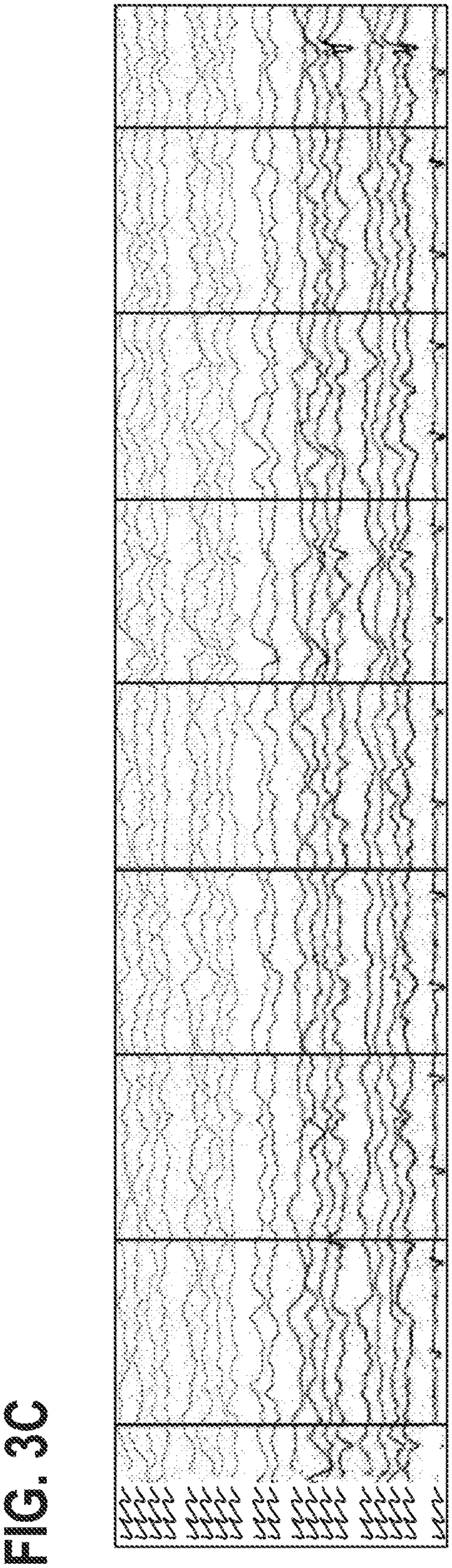

FIGS. 3A-3C show video EEGs in the patient described in Example 2 on day 1 (FIG. 3A), day 2 (FIG. 3B), and day 5 (FIG. 3C). FIG. 3A the EEG on day 1 demonstrates the return of electroclinical seizure arising from the right centrotemporal region on day 1, approximately 4 hours after pentobarbital drip was discontinued and as the study drug began. Double banana bipolar montage: LFF 1 Hz, HFF 70 Hz; sensitivity, 15 μV/mm; time base, 30 mm/s. EEG, electroencephalogram; HFF, high-frequency filter; LFF, low-frequency filter. FIG. 3B the EEG demonstrates isolated electroclinical seizure into day 3 of protocol as rhythmic fast polyspikes arising from bifrontal regions, which spread anteriorly over both hemispheres. Double banana bipolar montage: LFF 1 Hz, HFF 70 Hz; sensitivity, 15 μV/mm; time base, 30 mm/s. EEG, electroencephalogram; HFF, high-frequency filter; LFF, low-frequency filter. FIG. 3C the EEG demonstrates cessation of seizures on day 5 of protocol when transitioned from IV to enteric GNX with resolution of seizures, improvement in interictal background, and interictal right occipital epileptiform discharges. Double banana bipolar montage: LFF 1 Hz, HFF 70 Hz; sensitivity, 15 μV/mm; time base, 30 mm/s. EEG, electroencephalogram; HFF, high-frequency filter; LFF, low-frequency filter.

Figure 4:
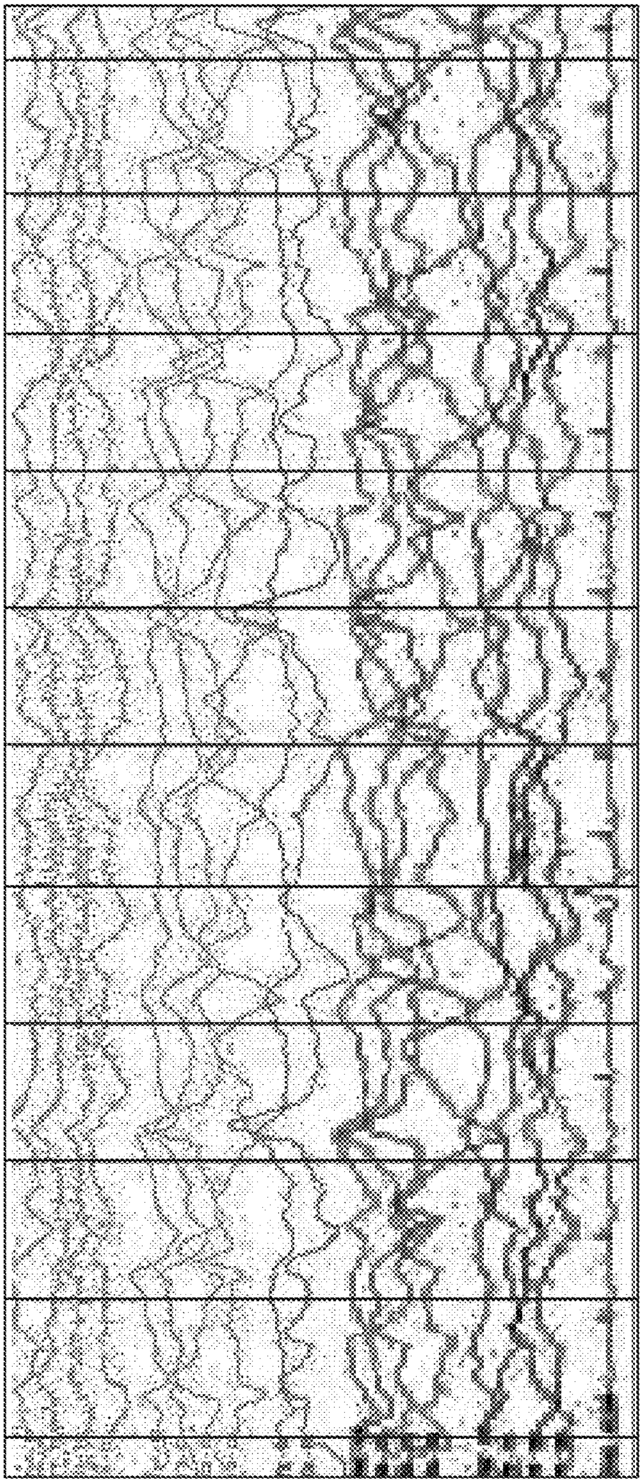
Figure 5:
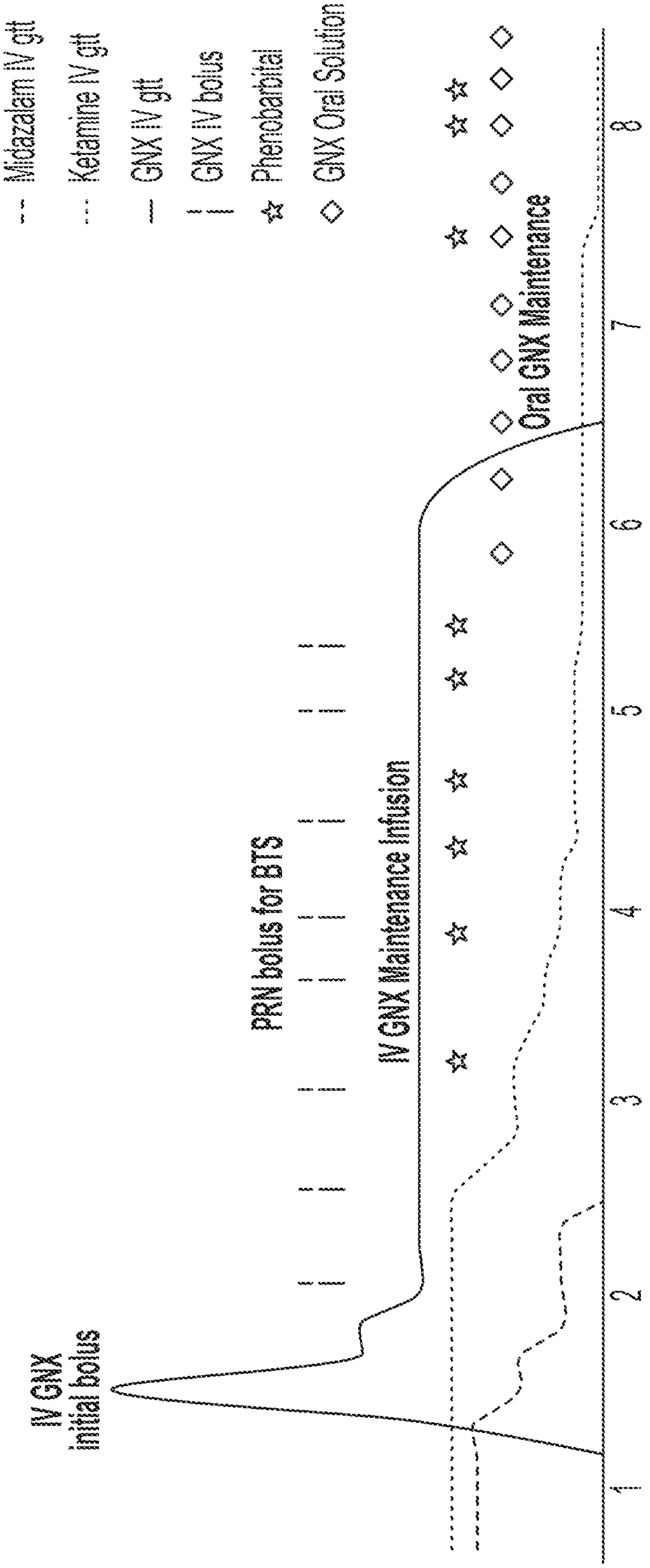

FIG. 4 shows an EEG of the patient described in Example 4 upon admission. This EEG demonstrates diffuse background slowing with epileptiform discharges in the biposterior head regions. Double banana bipolar montage: LFF 1 Hz, HFF 70 Hz; sensitivity, 15 μV/mm; time base, 30 mm/s. EEG, electroencephalogram; HFF, high-frequency filter; LFF, low frequency filter; PT, patient FIG. 5 shows the ganaxolone dosing regimen in the patient described in Example 4.

Figure 6A:
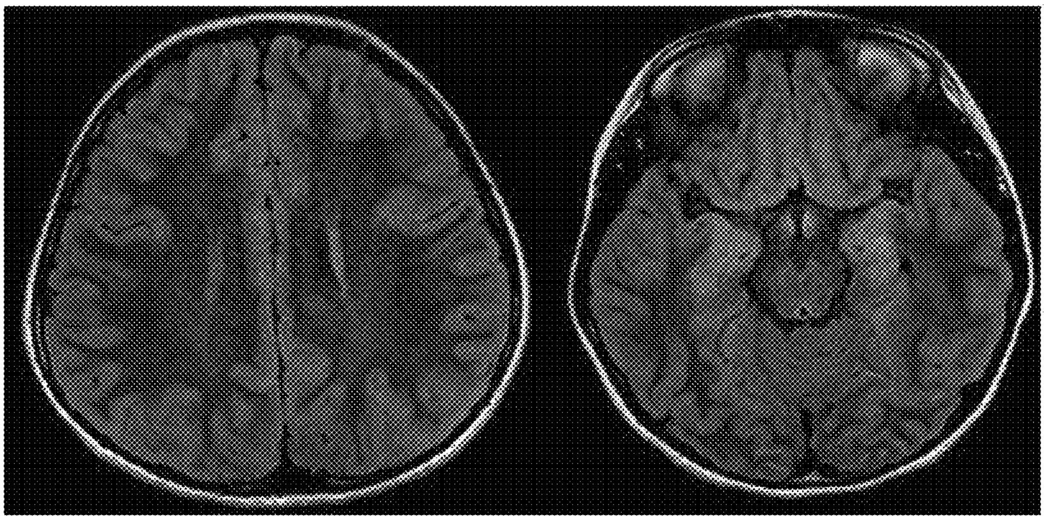
Figure 6B:
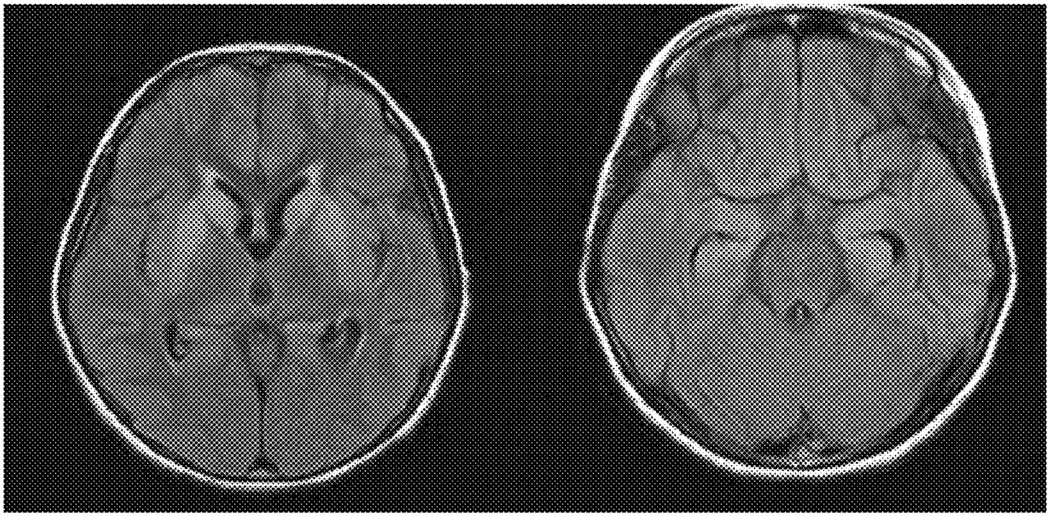
Figure 6C:
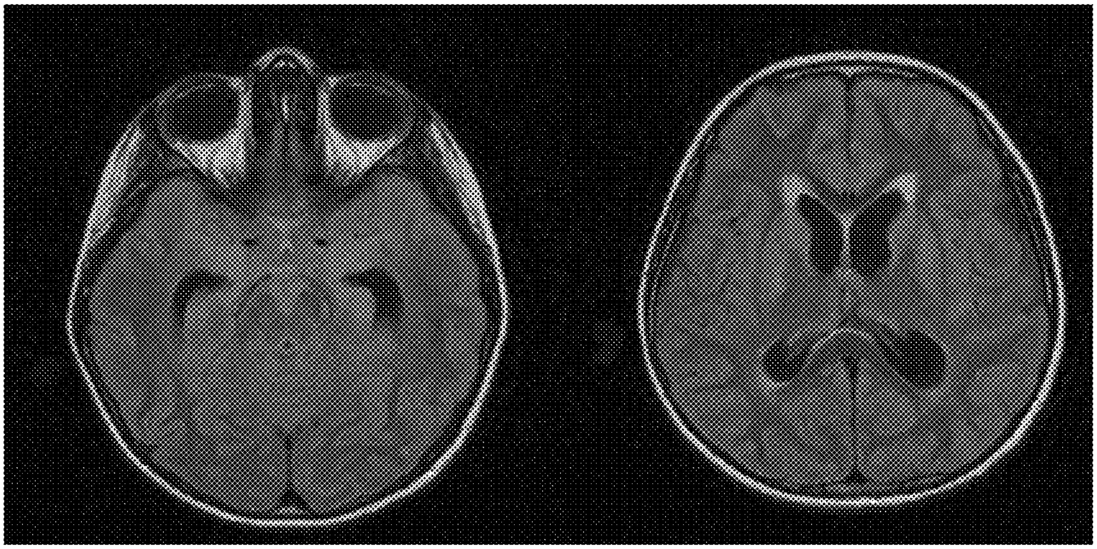

FIGS. 6A-6C show MRIs from the patient described in Example 4 at day 1 on admission (FIG. 6A), day 20 during ganaxolone infusion (FIG. 6B), and at 5.5 weeks post admission (FIG. 6C). FIG. 6A shows flair changes in bilateral temporal lobes. FIG. 6B shows continued flair changes/hyperintensities of gray matter-temporal lobe and basal ganglia. FIG. 6C shows atrophy.

4. DETAILED DESCRIPTION

SRSE patients are severely ill with a poor prognosis. SRSE occurs in about 23% to 43% of patients with SE. Up to half of these patients die and the others recover, but experience with neurological or other deficits. Currently, there are no therapies specifically approved for SRSE. Moreover, some recent attempts to develop new treatments have failed. There is clearly a need for improved methods for treating SRSE.

This disclosure relates to a new method for treating SRSE. As exemplified and described herein, treatment according to the method provides rapid SE suppression, and also provides for continued suppression of SE.

SRSE is defined as SE that continues or recurs 24 or more hours after the onset of anesthetic therapy, including cases where SE recurs on the reduction or withdrawal of anesthesia. In SRSE, one or more third-line agents such as pentobarbital, midazolam and propofol are administered at anesthetic doses to induce coma that is maintained for 24 hours or longer.

Suppression of SRSE typically breaks the seizures (i.e., suppresses or reduces seizure activity). Clinically, suppression of SRSE can be reduction in seizure burden (i.e., the percent of time during which there is electrographic seizure activity) and/or unacceptable ictal activity. For instance, a clinician may consider a seizure burden less than 20% to be suppression of SE and/or a seizure burden that is at least 50% less than during the 30 minutes prior to the initiation of treatment. Conventional treatment then slowly weans the subject off anesthetic agents to evaluate whether SE recurs on the reduction or withdrawal of anesthesia.

The methods described herein comprise rapidly weaning the patient off anesthetic agents until unacceptable ictal activity (e.g., seizure activity) returns, then initiating treatment with ganaxolone, for example as a bolus plus continuous infusion, to maintain plasma concentration of ganaxolone that manages ictal activity (e.g., suppresses SE) while continuing to wean the patient off anesthetic. The anesthetic agent is rapidly weaned by reducing the anesthetic agent by about 20% and preferably up to 30% at about 8 hour intervals. The inventors determined that seizure activity is typically considered unacceptable when the subject has an EEG ictal burden of about 20% for at least about 30 minutes as defined by the modified Salzburg criteria. At this point, treatment with an effective amount of a neurosteroid (e.g., ganaxolone) is typically initiated, for example as an intravenous bolus and a continuous intravenous infusion is initiated.

The intravenous bolus of ganaxolone is administered in an amount that is sufficient to suppress SE. Typically, a neurosteroid (e.g. ganaxolone) plasma concentration of about 800 ng/ml to about 1200 ng/ml is sufficient to suppress SE. For example, to achieve a ganaxolone plasma concentration of about 800 ng/ml to about 1200 ng/ml, about 30 mg bolus of ganaxolone can be administered.

Treatment according to the method lasts for a treatment period, which includes a period during which the continuous intravenous infusion is administered to maintain the subject's serum concentration of neurosteroid (e.g., ganaxolone) at or about a target level (i.e., a target concentration period), and periods during which the subjects plasma concentration of neurosteroid (e.g., ganaxolone) is allowed to or caused to fall below the target concentration, and a taper period during which the patient is weaned off the neurosteroid. The continuous intravenous infusion of neurosteroid (e.g. ganaxolone) is administered for a target concentration period in an amount sufficient for continued suppression of SE. Continued suppression of SE is achieved when the continuous infusion maintains a plasma concentration of neurosteroid (e.g. ganaxolone) of about 800 ng/ml or higher throughout the target concentration period. The target concentration period is typically at least about 2 hours, at least about 5 hours, and up to 5 days, although it is possible that the target concentration period can be longer in some subjects. During the target concentration period, the amount of neurosteroid (e.g. ganaxolone) administered to the subject (i.e., by the continuous intravenous infusion) can be increased or decreased to maintain continued suppression of SE, but is sufficient to maintain a plasma concentration of ganaxolone in the subject of at least about 800 ng/ml for at least 2 hours, at least about 5 hours, and up to 5 days or longer following the administration of the intravenous bolus and, optionally throughout the treatment period. Typically, the amount of ganaxolone administered by the continuous intravenous infusion is decreased over a period of about 24 hours from the initiation of the intravenous infusion. For instance, the amount of ganaxolone administered to the subject can be decreased about 2 hours after the initiation of the continuous intravenous infusion, and then about 10 hours to about 14 hours after infusion. Surprisingly, SE continues to be suppressed by the continuous intravenous infusion even though the amount of neurosteroid (e.g. ganaxolone) administered during the continuous intravenous infusion is decreased during the treatment period. As a result, the method provides enhanced safety and efficacy with lower exposure to ganaxolone than was expected. During treatment the subject can be monitored for plasma concentration of neurosteroid (e.g. ganaxolone) and using EEG to detect seizure activity. If the subject appears to show signs of SE relapse, the amount of ganaxolone administered can be adjusted accordingly. For instance, an additional intravenous bolus can be provided or the amount of ganaxolone infused can be increased. The amount of neurosteroid (e.g. ganaxolone) administered during infusion is typically adjusted by increasing or decreasing the infusion rate.

The continuous intravenous infusion is generally administered concurrently with the administration of the intravenous bolus. Although, in some cases, the continuous intravenous infusion can be initiated before or after the intravenous bolus.

The continuous intravenous infusion is typically followed by a taper period during which the subject is weaned off ganaxolone, typically over a period of about 12 hours. During the taper period the continuous intravenous infusion of ganaxolone is systematically decreased, typically by reducing the amount of ganaxolone that is administered to the subject (e.g., by the continuous intravenous infusion) by about one third every four hours until the subject no longer requires ganaxolone.

Additional description of the method and guidance for the practice of the method are provided herein. For ease of presentation, further details and guidance are provided with respect to a preferred aspect using ganaxolone. It is intended that the further details and guidance also relate to treatment with other neurosteroids.

A. Rapid Weaning

The method of treating SRSE comprises rapidly weaning the subject in need thereof off one or more anesthetic agents until unacceptable ictal activity (e.g., seizure) returns prior to the initiation of treatment with a neurosteroid, such as ganaxolone. As discussed herein, patients with SRSE typically have failed to respond to first-line benzodiazepines (typically lorazepam, diazepam, or midazolam) and second-line therapies (typically phenytoin/fosphenytoin, phenobarbital, levetiracetam or valproate), and one or more third-line anesthetic agents (typically pentobarbital, midazolam and propofol) are used to place the patient in a medically induced coma. Preferably, the subject is rapidly weaned off all anesthetic agents. Although, a prescribing clinician will recognize that in some instances the subject may benefit from continuing to be administered one or more anesthetic agents or other therapeutic agents. Without being bound by theory, the inventors believe that rapidly weaning the subject off the anesthetic agent and briefly allowing ictal activity (e.g., seizure) to return and then administering ganaxolone to manage ictal activity while continuing to actively withdraw anesthesia, maximizes ganaxolone exposure without the presence of anesthetics and hence reduces hyperexcitability induced by anesthetic agents. Ganaxolone can then be used to manage ictal activity and the patient can be weaned off ganaxolone without causing the hyperresponsiveness that is caused by withdrawing anesthetics.

The anesthetic agent can be rapidly weaned by reducing the anesthetic by at least about 20% and up to around 40% at desired intervals, such as about 8 hour intervals. In instances, the anesthetic is reduced by at least about 20%, at least about 25%, at least about 30%, at least about 35%, or at least about 40% at about 8 hour intervals. Shorter intervals, such as 1 hour, 2 hours, 3 hours, 4 hours, 5 hours, 6 hours, or 7 hours may be used. Alternatively, longer intervals such as 9 hours, 10 hours, 11 hours, 12 hours, 13 hours, 14 hours, or 15 hours may be used. Prior to and/or during weaning of an anesthetic agent, the subject typically has burst suppression.

Unacceptable ictal activity occurs when the subject has an EEG ictal burden of about 20% for at least 30 minutes as defined by the modified Salzburg criteria and/or no clear clinical improvement is observed. The subject may have increased epileptiform discharges or rhythmic delta/theta activity. At this point, treatment with ganaxolone is initiated typically at a high infusion dose of ganaxolone (such as a dose that achieves and maintains a ganaxolone serum concentration of at least about 800 ng/ml or 900 ng/ml). For example, ganaxolone can be administered as an intravenous bolus and a continuous intravenous infusion.

In some cases, the subject may not have been completely weaned off the anesthetic agent prior to the initiation of treatment with ganaxolone. In such cases, weaning of the anesthetic agent can be accelerated so that the subject is weaned off the anesthetic agent within 48 hours of initiation of treatment with ganaxolone. For example, anesthetic can be reduced by at least about 20%, at least about 25%, at least about 30%, at least about 35%, at least about 40%, at least about 50%, at least about 60%, at least about 70% or more at intervals from about 0.5 hours, 1 hours, 2 hours, 3 hours, 4 hours, 5 hours, or longer until the subject is no longer administered an anesthetic agent.

It is common for one or more third-line anesthetic agents (typically pentobarbital, midazolam and propofol) to be used to place the patient in a medically induced coma. When the subject has been administered more than one anesthetic agent, the subject can be weaned off individual anesthetic agents or the combination of anesthetic agents. For example, the patient can be weaned off one anesthetic agent while the patient continues to be administered of one or more different anesthetic agents. Preferably, barbiturates are the first anesthetic agent to be reduced and discontinued, followed by benzodiazepines, and then propofol. In some instances, treatment with ketamine can continue throughout the treatment period with ganaxolone. It may be desirable to continue treatment with a second-line anti-epileptic drug. Preferably, the second-line anti-epileptic agent targets a different mechanism to ganaxolone. The second-line anti-epileptic agent when administered is preferably administered on a different schedule to ganaxolone.

B. Ganaxolone Administration

Generally, ganaxolone is administered when the subject has been rapidly weaned off the anesthetic agents until ictal activity that is not considered to be tolerable is observed typically by infusion of ganaxolone at a high infusion dose (such as a dose that achieves and maintains a ganaxolone serum concentration of at least about 800 ng/ml or 900 ng/ml) for at least about 2.5 hours and up to about 5 days to suppress unacceptable ictal activity (e.g., SE and/or seizure) and permit withdrawal of anesthetic. For example, ganaxolone can be administered to the subject for at least about 24 hours, about 36 hours, about 48 hours, about 72 hours, about 96 hours, about 4 days, about 5 days or more (e.g., 6 days, 7 days, 8 days, 9 days, 10 days). Preferably, ganaxolone is administered for about 36 hours up to about 5 days. If desired the amount of ganaxolone that is administered can be reduced after the initial about 2.5 hours, but typically will be sufficient to suppress SRSE break through (e.g., an amount that achieves and maintains a ganaxolone serum concentration of at least about 400 ng/ml, at least about 500 ng/ml, at least about 600 ng/ml or higher). For example, ganaxolone can be administered as a bolus plus continuous intravenous infusion, which is discussed in more detail below.

i. Intravenous Bolus

The method for treating SRSE can comprise administering to a subject in need thereof an intravenous bolus of ganaxolone in an amount sufficient to suppress unacceptable ictal activity (e.g., SE), which typically is an amount sufficient to produce a ganaxolone plasma concentration of at least about 800 ng/ml to about 1200 ng/ml. Typically the intravenous bolus results in a ganaxolone plasma concentration of about 800 ng/ml to about 1200 ng/ml.

For example, the intravenous bolus of ganaxolone can include an amount of ganaxolone that is sufficient to achieve a ganaxolone plasma concentration of at least about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1000 ng/ml, about 1025 ng/ml, about 1050 ng/ml, about 1075 ng/ml, about 1100 ng/ml, about 1200 ng/ml. Preferably, the intravenous bolus achieves a ganaxolone plasma concentration of at least about 800 ng/ml to about 1200 ng/ml.

While a ganaxolone plasma concentration of at least about 800 ng/ml to about 1200 ng/ml is preferable to suppress SRSE, there can be some variability based on, for example a differences in subjects' weight, metabolism, age, duration of SRSE and/or severity of SRSE. Accordingly, a skilled clinician will understand that lower exposure to ganaxolone, such as a plasma concentration of at least about 425 ng/ml, at least about 450 ng/ml, at least about 475 ng/ml, at least about 500 ng/ml, at least about 525 ng/ml, at least about 550 ng/ml, at least about 600 ng/ml, at least about 650 ng/ml, at least 700 ng/ml, at least 725 ng/ml, at least 750 ng/ml, or at least 775 ng/ml could suppress SE in some SRSE patients. Alternatively, a skilled clinician will understand that a higher exposure to ganaxolone, such as a plasma concentration of at least about 1000 ng/ml, at least about 1050 ng/ml, at least about 1100 ng/ml, or at least about 1200 ng/ml, would be needed to suppress SE in some SRSE patients. However, it is preferred that the bolus delivers an amount of ganaxolone that is sufficient to achieve a plasma concentration of ganaxolone of about 1000 ng/ml. A plasma concentration of ganaxolone above about 1000 ng/ml can induce anesthesia in a subject, which is generally not an intended effect or desired outcome of the methods described herein. Preferably, the intravenous bolus of ganaxolone results in minimal or no anesthetic effects. For example, preferably, the amount of ganaxolone administered does not result in loss of consciousness, does not result in paralysis, and/or does not cause deep sedation. Preferably, treatment in accordance with the methods described herein does not require the subject to undergo controlled ventilation and/or endotracheal intubation.

In some instances, a plasma concentration of about 1005 ng/ml, about 1010 ng/ml, 1020 ng/ml, 1030 ng/ml, 1040 ng/ml, 1050 ng/ml, 1060 ng/ml, 1070 ng/ml, 1080 ng/ml, can be achieved to suppress SE without resulting in anesthesia. In other instances, a ganaxolone plasma concentration that is greater than 1000 ng/ml by about 1%, about 2%, about 3%, about 4%, about 5%, about 6%, about 7%, about 8%, about 9%, about 10%, about 11%, about 12%, about 13%, about 14%, or about 15% can be sufficient to suppress SE without resulting in anesthesia.

The intravenous bolus of ganaxolone can be administered (i.e., infused) into the subject at an amount of about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg. Preferably, about 30 mg of ganaxolone is infused into the subject during the intravenous bolus.

In subjects' weighing less than about 40 kg, about 0.10 mg/kg, about 0.11 mg/kg, about 0.12 mg/kg, about 0.13 mg/kg, about 0.14 mg/kg, about 0.15 mg/kg, about 0.16 mg/kg, about 0.17 mg/kg, about 0.18 mg/kg, about 0.19 mg/kg, about 0.20 mg/kg, about 0.21 mg/kg, about 0.22 mg/kg, about 0.23 mg/kg, about 0.24 mg/kg, about 0.25 mg/kg, about 0.26 mg/kg, about 0.27 mg/kg, about 0.28 mg/kg, about 0.29 mg/kg, about 0.30 mg/kg, about 0.31 mg/kg, about 0.32 mg/kg, about 0.33 mg/kg, about 0.34 mg/kg, about 0.35 mg/kg, about 0.36 mg/kg, about 0.37 mg/kg, about 0.38 mg/kg, about 0.39 mg/kg, about 0.40 mg/kg, about 0.41 mg/kg, about 0.42 mg/kg, about 0.43 mg/kg, about 0.44 mg/kg, about 0.45 mg/kg, about 0.46 mg/kg, about 0.47 mg/kg, about 0.48 mg/kg, about 0.49 mg/kg, about 0.5 mg/kg, about 0.51 mg/kg, about 0.52 mg/kg, about 0.53 mg/kg, about 0.54 mg/kg, about 0.55 mg/kg, about 0.56 mg/kg, about 0.57 mg/kg, about 0.58 mg/kg, about 0.59 mg/kg, about 0.60 mg/kg, about 0.61 mg/kg, about 0.62 mg/kg, about 0.63 mg/kg, about 0.64 mg/kg, about 0.65 mg/kg, about 0.66 mg/kg, about 0.67 mg/kg, about 0.68 mg/kg, about 0.69 mg/kg, about 0.7 mg/kg, about 0.75 mg/kg, about 0.80 mg/kg, about 0.85 mg/kg, about 0.90 mg/kg, about 0.95 mg/kg of ganaxolone can be infused into the subject during the intravenous bolus. Preferably, about 0.43 mg/kg of ganaxolone is infused into the subject during the intravenous bolus. Preferably, about 0.75 mg/kg of ganaxolone is infused into the subject during the intravenous bolus.

The intravenous bolus can be administered to the subject for any desired period of time and is typically administered from about 1 minute to about 10 minutes, such as, from about 1 minute to about 5 minutes, about 1 minute to about 4 minutes, about 1 minute to about 3 minutes, about 1 minute to about 2 minutes, about 2 minutes to about 5 minutes, about 2 minutes to about 4 minutes, about 2 minutes to about 3 minutes, about 3 minutes to about 5 minutes, or about 3 minutes to about 4 minutes. The intravenous bolus can preferably be administered to the subject for about 1 minute, about 2 minutes, about 3 minutes, or about 5 minutes. More preferably, the intravenous bolus is administered to the subject for about 3 minutes.

In instances when a ganaxolone plasma concentration of at least about 800 ng/ml is not achieved after the intravenous bolus of ganaxolone, the subject may be administered an additional intravenous bolus of ganaxolone to achieve a ganaxolone plasma concentration of at least about 800 ng/ml, and preferably about 1200 ng/ml.

C. Continuous Intravenous Infusion

The continuous intravenous infusion of ganaxolone can be administered periprocedural with the intravenous bolus. For instance, the continuous intravenous infusion can be initiated concurrently with the administration of the intravenous bolus. Alternatively, the continuous intravenous infusion can be initiated before or after the administration of the intravenous bolus. Typically, the intravenous infusion and continuous intravenous infusion is administered from the same ganaxolone source (e.g., and intravenous bag connect to IV line) and are initiated concurrently. The continuous intravenous infusion of ganaxolone is administered in an amount to continue SE suppression throughout the treatment period and beyond. The continuous intravenous infusion of ganaxolone provides durable suppression of SE that lasts preferably through the treatment period, preferably through the taper period, preferably after the taper period, and preferably post-treatment.

In embodiments, the continuous intravenous infusion of ganaxolone achieves suppression of SE for at least 1 hour, at least 2 hours, at least 3 hours, at least 4 hours, at least 5 hours, at least 6 hours at least 7 hours, at least 8 hours, at least 9 hours, at least 10 hours, at least 11 hours, at least 12 hours, at least 1 day, at least 2 days, at least 3 days, at least 4 days, at least 5 days, at least 6 days, at least 7 days or longer post-treatment. In embodiments, the continuous intravenous infusion of ganaxolone achieves suppression of SE for at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks or longer post-treatment. In embodiments, the continuous intravenous infusion of ganaxolone achieves suppression of SE for at least 1 month, at least 2 months, at least 3 months, at least 4 months, at least 5 months, at least 6 months, at least 7 months, at least 8 months, at least 9 months, at least 10 months, at least 11 months, at least 12 months or longer post-treatment.

Continued SE suppression is achieved by administering to the subject a continuous intravenous infusion in an amount sufficient to produce a ganaxolone plasma concentration of at least about 800 ng/ml for a target concentration period, which typically is at least about 2.5 hours, at least about 5 hours and up to 5 days or longer, following the administration of the intravenous bolus, and optionally throughout the treatment period (e.g., up to 96 hours or longer). For example, ganaxolone can be administered to the subject for at least about 24 hours, about 36 hours, about 48 hours, about 72 hours, about 96 hours, about 4 days, about 5 days or more (e.g., 6 days, 7 days, 8 days, 9 days, 10 days). Preferably, ganaxolone is administered for about 36 hours up to about 5 days.

In practice, the patient's plasma concentration of ganaxolone can be monitored and the amount of ganaxolone that is infused can be adjusted or titrated to maintain a plasma concentration of at least about 800 ng/ml throughout the treatment period. A ganaxolone plasma concentration of at least about 800 ng/ml period, for example for about 2 hours, about 3 hours, about 4 hours, about 5 hours about 6 hours, about 7 hours, about 8 hours, about 9 hours, about 10 hours, about 11 hours, about 12 hours, about 24 hours, about 36 hours, about 72 hours, about 96 hours or longer can achieve continued SE suppression.

The continuous intravenous infusion of ganaxolone can be administered to the subject in an amount to achieve a ganaxolone plasma concentration of about 800 ng/ml to about 1200 ng/ml for at least 2.5 hours, at least about 5 hours, and up to 5 days or longer. For example, ganaxolone can be administered to the subject for at least about 24 hours, about 36 hours, about 48 hours, about 72 hours, about 96 hours, about 4 days, about 5 days or more (e.g., 6 days, 7 days, 8 days, 9 days, 10 days). Preferably, ganaxolone is administered for about 36 hours up to about 5 days. While a plasma concentration of at least about 800 ng/ml is preferable for continued SE suppression, there can be some variability based on, for example, differences in subjects' weight, metabolism, age, duration of SE and/or severity of SE. Accordingly, a skilled clinician will understand that, for example, a ganaxolone plasma concentration of at least about 425 ng/ml, at least about 450 ng/ml, at least about 475 ng/ml, at least about 500 ng/ml, at least about 525 ng/ml, at least about 550 ng/ml, at least about 600 ng/ml, at least about 650 ng/ml, at least 700 ng/ml, at least 725 ng/ml, at least 750 ng/ml, or at least 775 ng/ml can be sufficient for continued SE suppression in some SE subjects. A skilled clinician will also understand that in some patients a higher exposure to ganaxolone, such as a plasma concentration of at least about 1000 ng/ml, at least about 1050 ng/ml, at least about 1100 ng/ml, or at least about 1200 ng/ml, would be needed to suppress SE in some SRSE patients.

A ganaxolone plasma concentration less than 400 ng/ml or less than 500 ng/ml will typically not be sufficient for continued SE suppression. In embodiments, the continuous intravenous infusion of ganaxolone achieves a ganaxolone plasma concentration of about 425 ng/ml, about 450 ng/ml, about 475 ng/ml, about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1000 ng/ml, about 1025 ng/ml, about 1050 ng/ml, about 1075 ng/ml, about 1100 ng/ml, at least about 1150 ng/ml, or at least about 1200 ng/ml. Preferably, a ganaxolone plasma concentration of about 800 ng/ml to about 1000 ng/ml is desired.

A plasma concentration of ganaxolone above about 1000 ng/ml can induce anesthesia in a subject, which is generally not an intended effect or desired outcome of the methods described herein. Preferably, the continuous intravenous infusion of ganaxolone results in minimal or no anesthetic effects. For example, preferably, the amount of ganaxolone administered does not result in loss of consciousness, does not result in paralysis, and/or does not cause deep sedation. Preferably, treatment in accordance with the methods described herein does not require the subject to undergo controlled ventilation and/or endotracheal intubation.

In some instances, a ganaxolone plasma concentration of about 1005 ng/ml, about 1010 ng/ml, 1020 ng/ml, 1030 ng/ml, 1040 ng/ml, 1050 ng/ml, 1060 ng/ml, 1070 ng/ml, 1080 ng/ml, 1090 ng/ml, 1100 ng/ml, 1110 ng/ml, 1120 ng/ml, 1130 ng/ml, 1140 ng/ml, 1150 ng/ml, 1160 ng/ml, 1170 ng/ml, 1180 ng/ml, 1190 ng/ml, or 1200 ng/ml can result in continued SE suppression without causing anesthesia. In instances, a ganaxolone plasma concentration less than about 1%, less than about 2%, less than about 3%, less than about 4%, less than about 5%, less than about 6%, less than about 7%, less than about 8%, less than about 9%, less than about 10%, less than about 11%, less than about 12%, less than about 13%, less than about 14%, or less than about 15% of 500 ng/ml can be sufficient to suppress SE. In other instances, a ganaxolone plasma concentration greater about 1%, than about 2%, bout 3%, about 4%, about 5%, about 6%, about 7%, about 8%, about 9%, about 10%, about 11%, about 12%, about 13%, about 14%, about 15%, or about 20% of 1000 ng/ml can be sufficient for continued SE suppression without resulting in anesthesia.

The amount of ganaxolone administered to the subject per hour by continuous intravenous infusion can be decreased over the continuous intravenous infusion treatment period, but typically will be sufficient to suppress SRSE breakthrough (e.g., an amount that achieves and maintains a ganaxolone serum concentration of at least about 400 ng/ml, at least about 500 ng/ml, at least 600 ng/ml or higher). In instances, the continuous intravenous infusion can be decreased over a period of about 24 hours from the initiation of the intravenous infusion. For example, the amount of ganaxolone administered to the subject per hour by continuous intravenous infusion can be decreased about 1 hour, about 1.5 hours, about 2 hours, about 2.5 hours, about 3 hours, about 3.5 hours, about 4 hours, about 4.5 hours, about 5 hours, about 6 hours, about 7 hours, about 8 hours, about 9 hours, about 10 hours, about 11 hours, about 12 hours, about 14 hours, about 15 hours, about 16 hours, about 17 hours, about 18 hours, about 19 hours, about 20 hours, about 21 hours, about 22 hours, about 23 hours, or about 24 hours after the initiation of the continuous intravenous infusion.

The amount of ganaxolone administered to the subject per hour by continuous intravenous infusion can be decreased or further decreased at one or more periods over the continuous intravenous infusion treatment period. For example, the amount of ganaxolone administered to the subject per hour by continuous intravenous infusion can be decreased at one interval, two intervals, three intervals, four intervals, five intervals or more during the continuous intravenous infusion treatment period. In the methods provided herein, the amount of ganaxolone administered to the subject per hour by continuous intravenous infusion is preferably decreased at two time intervals over about 24 hours from the initiation of the continuous intravenous infusion.

The amount of ganaxolone administered to the subject per hour by continuous intravenous infusion can be deceased or further decreased between about 1 hours to about 5 hours, about 1 hour to about 4 hours, about 1 hour to about 3 hours, about 2 hours to about 3 hours, about 2 hours to about 4 hours, about 2 hours to about 4 hours, about 2 hours to about 5 hours, about 3 hours to about 4 hours, about 4 hours to about 5 hours after the initiation of the continuous intravenous infusion. The amount of ganaxolone administered to the subject per hour by continuous intravenous infusion is preferably decreased about 2 hours after the initiation of the continuous intravenous infusion.

The amount of ganaxolone administered to the subject per hour by continuous intravenous infusion can be decreased or further decreased about 8 hours to about 16 hours, about 8 hours to about 15 hours, about 8 hours to about 14 hours, about 8 hours to about 13 hours, about 8 hours to about 12 hours, about 8 hours to about 11 hours, about 8 hours to about 10 hours, about 9 hours to about 16 hours, about 9 hours to about 15 hours, about 9 hours to about 14 hours, about 9 hours to about 13 hours, about 9 hours to about 12 hours, about 9 hours to about 11 hours, about 9 hours to about 10 hours, about 10 hours to 16 hours, about 10 hours to about 15 hours, about 10 hours to about 14 hours, about 10 hours to about 13 hours, about 10 hours to about 12 hours, about 10 hours to about 11 hours after the initiation of the continuous intravenous infusion. The amount of ganaxolone administered to the subject per hour by continuous intravenous infusion is preferably decreased at about 10 hours to about 14 hours after the initiation of the continuous intravenous infusion. More specifically, the amount of ganaxolone administered to the subject per hour by continuous intravenous infusion is decreased at about 12 hours after the initiation of the continuous intravenous infusion.

The amount of ganaxolone administered to the subject per hour by continuous intravenous infusion can be decreased between about 1 hours to about 5 hours, about 1 hour to about 4 hours, about 1 hour to about 3 hours, about 2 hours to about 3 hours, about 2 hours to about 4 hours, about 2 hours to about 4 hours, about 2 hours to about 5 hours, about 3 hours to about 4 hours, about 4 hours to about 5 hours after the initiation of the continuous intravenous infusion, and then about 8 hours to about 16 hours, about 8 hours to about 15 hours, about 8 hours to about 14 hours, about 8 hours to about 13 hours, about 8 hours to about 12 hours, about 8 hours to about 11 hours, about 8 hours to about 10 hours, about 9 hours to about 16 hours, about 9 hours to about 15 hours, about 9 hours to about 14 hours, about 9 hours to about 13 hours, about 9 hours to about 12 hours, about 9 hours to about 11 hours, about 9 hours to about 10 hours, about 10 hours to 16 hours, about 10 hours to about 15 hours, about 10 hours to about 14 hours, about 10 hours to about 13 hours, about 10 hours to about 12 hours, about 10 hours to about 11 hours after the initiation of the continuous intravenous infusion.

The amount of ganaxolone administered to the subject per hour by continuous intravenous infusion is preferably decreased at about 2 hours after the initiation of the continuous intravenous infusion, and then about 10 hours to about 14 hours after the initiation of the continuous intravenous infusion.

The amount of ganaxolone administered to the subject per hour by continuous intravenous infusion can be decreased by about 40%, about 45%, about 50%, about 55%, about 60%, about 65%, about 70%, about 75%, about 80%, about 85%, or about 90% relative to the amount administered per hour at the initiation of the continuous intravenous infusion.

In embodiments, the amount of ganaxolone administered to the subject per hour by continuous intravenous infusion can be decreased by about 40%, about 45%, about 50%, about 55%, about 65%, about 60%, about 70% about 75%, about 80%, about 85%, or about 90%, relative to the amount administered per hour at the initiation of the continuous intravenous infusion, about 1 hour, about 1.5 hours, about 2 hours, about 2.5 hours, about 3 hours, about 3.5 hours, about 4 hours, about 4.5 hours, about 5 hours, about 6 hours, about 7 hours, about 8 hours, about 9 hours, about 10 hours, about 11 hours, about 12 hours, about 14 hours, about 15 hours, about 16 hours, about 17 hours, about 18 hours, about 19 hours, about 20 hours, about 21 hours, about 22 hours, about 23 hours, or about 24 hours after the initiation of the continuous intravenous infusion.

The amount of ganaxolone administered to the subject per hour by continuous intravenous infusion can be decreased by about 40%, about 45%, about 50%, about 55%, or about 60% relative to the amount administered per hour at the initiation of the continuous intravenous infusion, about 1 hour to about 5 hours after the initiation of the continuous intravenous infusion. The amount of ganaxolone administered to the subject per hour by continuous intravenous is preferably decreased by about 50%, relative to the amount administered per hour at the initiation of the continuous intravenous infusion, about 2 hours after the initiation of the continuous intravenous infusion.

The amount of ganaxolone administered to the subject per hour by continuous intravenous infusion can be decreased by about 50%, about 55%, about 60%, about 65%, about 70%, about 75%, about 80%, or about 85% relative to the amount administered per hour at the initiation of the continuous intravenous infusion, about 10 hours to about 14 hours after the initiation of the continuous intravenous infusion. The amount of ganaxolone administered to the subject per hour by continuous intravenous infusion is preferably decreased by about 75%, relative to the amount administered per hour at the initiation of the continuous intravenous infusion, about 10 hours after the initiation of the continuous intravenous infusion.

The continuous intravenous infusion comprises infusing into the subject about 10 mg, about 15 mg, about 20 mg, about 25 mg, about 30 mg, about 35 mg, about 40 mg, about 45 mg, about 50 mg, about 60 mg, about 65 mg, about 70 mg, about 80 mg, about 85 mg, about 90 mg, about 95 mg, or about 100 mg of ganaxolone per hour during the continuous intravenous infusion. Preferably, the continuous intravenous infusion comprises infusing into the subject about 20 mg of ganaxolone per hour to about 80 mg of ganaxolone per hour during the continuous infusion treatment period.

In subjects weight less than about 40 kg, the continuous intravenous infusion comprises infusion into the subject about 0.10 mg/kg, about 0.11 mg/kg, about 0.12 mg/kg, about 0.13 mg/kg, about 0.14 mg/kg, about 0.15 mg/kg, about 0.16 mg/kg, about 0.17 mg/kg, about 0.18 mg/kg, about 0.19 mg/kg, about 0.20 mg/kg, about 0.21 mg/kg, about 0.22 mg/kg, about 0.23 mg/kg, about 0.24 mg/kg, about 0.25 mg/kg, about 0.26 mg/kg, about 0.27 mg/kg, about 0.28 mg/kg, about 0.29 mg/kg, about 0.30 mg/kg, about 0.31 mg/kg, about 0.32 mg/kg, about 0.33 mg/kg, about 0.34 mg/kg, about 0.35 mg/kg, about 0.36 mg/kg, about 0.37 mg/kg, about 0.38 mg/kg, about 0.39 mg/kg, about 0.40 mg/kg, about 0.41 mg/kg, about 0.42 mg/kg, about 0.43 mg/kg, about 0.44 mg/kg, about 0.45 mg/kg, about 0.46 mg/kg, about 0.47 mg/kg, about 0.48 mg/kg, about 0.49 mg/kg, about 0.5 mg/kg, about 0.51 mg/kg, about 0.52 mg/kg, about 0.53 mg/kg, about 0.54 mg/kg, about 0.55 mg/kg, about 0.56 mg/kg, about 0.57 mg/kg, about 0.58 mg/kg, about 0.59 mg/kg, about 0.60 mg/kg, about 0.61 mg/kg, about 0.62 mg/kg, about 0.63 mg/kg, about 0.64 mg/kg, about 0.65 mg/kg, about 0.66 mg/kg, about 0.67 mg/kg, about 0.68 mg/kg, about 0.69 mg/kg, about 0.7 mg/kg, about 0.75 mg/kg, about 0.80 mg/kg, about 0.85 mg/kg, about 0.90 mg/kg, about 0.95 mg/kg, about 1.0 mg/kg, about 1.10 mg/kg, about 1.11 mg/kg, about 1.12 mg/kg, about 1.13 mg/kg, about 1.14 mg/kg, about 1.15 mg/kg, about 1.16 mg/kg, about 1.17 mg/kg, about 1.18 mg/kg, about 1.19 mg/kg, about 1.20 mg/kg, about 1.21 mg/kg, about 1.22 mg/kg, about 1.23 mg/kg, about 1.24 mg/kg, about 1.25 mg/kg, about 1.26 mg/kg, about 1.27 mg/kg, about 1.28 mg/kg, about 1.29 mg/kg, about 1.30 mg/kg, about 1.31 mg/kg, about 1.32 mg/kg, about 1.33 mg/kg, about 1.34 mg/kg, about 1.35 mg/kg, about 1.36 mg/kg, about 1.37 mg/kg, about 1.38 mg/kg, about 1.39 mg/kg, about 1.40 mg/kg, about 1.41 mg/kg, about 1.42 mg/kg, about 1.43 mg/kg, about 1.44 mg/kg, about 1.45 mg/kg, about 1.46 mg/kg, about 1.47 mg/kg, about 1.48 mg/kg, about 1.49 mg/kg, about 1.50 mg/kg, about 1.51 mg/kg, about 1.52 mg/kg, about 1.53 mg/kg, about 1.54 mg/kg, about 1.55 mg/kg, about 1.56 mg/kg, about 1.57 mg/kg, about 1.58 mg/kg, about 1.59 mg/kg, about 1.60 mg/kg, about 1.61 mg/kg, about 1.62 mg/kg, about 1.63 mg/kg, about 1.64 mg/kg, about 1.65 mg/kg, about 1.66 mg/kg, about 1.67 mg/kg, about 1.68 mg/kg, about 1.69 mg/kg, about 1.70 mg/kg, about 1.71 mg/kg, about 1.72 mg/kg, about 1.73 mg/kg, about 1.74 mg/kg, about 1.75 mg/kg, about 1.76 mg/kg, about 1.77 mg/kg, about 1.78 mg/kg, about 1.79 mg/kg, about 1.80 mg/kg, about 1.81 mg/kg, about 1.82 mg/kg, about 1.83 mg/kg, about 1.84 mg/kg, about 1.85 mg/kg, about 1.86 mg/kg, about 1.87 mg/kg, about 1.88 mg/kg, about 1.89 mg/kg, about 1.90 mg/kg, about 1.91 mg/kg, about 1.92 mg/kg, about 1.93 mg/kg, about 1.94 mg/kg, about 1.95 mg/kg, about 1.96 mg/kg, about 1.97 mg/kg, about 1.98 mg/kg, about 1.99 mg/kg, or about 2.0 mg/kg of ganaxolone can be infused into the subject during the intravenous bolus. Preferably, the continuous intravenous infusion comprises infusing into the subject weighing less than 40 kg about 0.2 mg/kg of ganaxolone per hour to about 1.2 mg/kg of ganaxolone per hour during the continuous infusion treatment period. Preferably, the continuous intravenous infusion comprises infusing into the subject weighing less than 40 kg about 0.2 mg/kg of ganaxolone per hour to about 2.0 mg/kg of ganaxolone per hour during the continuous infusion treatment period.

In embodiments, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, or about 89 mg, about 90 mg of ganaxolone are infused into the subject at the initiation of the continuous intravenous infusion. About 80 mg of ganaxolone per hour is preferably infused into the subject at the initiation of the continuous intravenous infusion. The amount of ganaxolone can then be decreased to about 60 mg, about 55 mg, about 40 mg, about 35 mg, about 30 mg, about 25 mg, about 20 mg, about 15 mg, or about 10 mg. Preferably the amount of ganaxolone is decreased to about 40 mg of ganaxolone and then about 35 mg of ganaxolone during the treatment period.

In embodiments, in subject's weight less than 40 kg, about 0.9 mg/kg, about 0.91 mg/kg, about 0.92 mg/kg, about 0.93 mg/kg, about 0.94 mg/kg, about 0.95 mg/kg, about 0.96 mg/kg, about 0.97 mg/kg, about 0.98 mg/kg, about 0.99 mg/kg, about 1.0 mg/kg, about 1.10 mg/kg, about 1.11 mg/kg, about 1.12 mg/kg, about 1.13 mg/kg, about 1.14 mg/kg, about 1.15 mg/kg, about 1.16 mg/kg, about 1.17 mg/kg, about 1.18 mg/kg, about 1.19 mg/kg, or about 1.20 mg/kg of ganaxolone per hour are infused into the subject at the initiation of the continuous intravenous infusion. About 1.14 mg/kg of ganaxolone per hour is preferably infused into the subject at the initiation of the continuous intravenous infusion. About 2.0 mg/kg of ganaxolone per hour is preferably infused into the subject at the initiation of the continuous intravenous infusion. The amount of ganaxolone can then be decreased to about 0.45 mg/kg, about 0.46 mg/kg, about 0.47 mg/kg, about 0.48 mg/kg, about 0.49 mg/kg, about 0.5 mg/kg, about 0.51 mg/kg, about 0.52 mg/kg, about 0.53 mg/kg, about 0.55 mg/kg, about 0.56 mg/kg, about 0.57 mg/kg, about 0.58 mg/kg, about 0.59 mg/kg, about 0.60 mg/kg, about 0.60 mg/kg, about 0.61 mg/kg, about 0.62 mg/kg, about 0.63 mg/kg, about 0.64 mg/kg, about 0.65 mg/kg, about 0.66 mg/kg, about 0.67 mg/kg, about 0.68 mg/kg, about 0.69 mg/kg, about 0.7 mg/kg, about 0.75 mg/kg, about 0.80 mg/kg, about 0.85 mg/kg, about 0.90 mg/kg, about 0.95 mg/kg, about 1.0 mg/kg, Preferably the amount of ganaxolone is decreased to about 0.57 mg/kg of ganaxolone and then about 0.29 mg/kg of ganaxolone during the treatment period. Preferably the amount of ganaxolone is decreased to about 1.0 mg/kg.

In embodiments, about 40 mg of ganaxolone per hour is administered to the subject by continuous intravenous infusion starting about 2 hours after initiation of the continuous intravenous infusion and for about 6 hours to about 10 hours thereafter. In embodiments, about 35 mg of ganaxolone per hour is administered to the subject by continuous intravenous infusion starting about 12 hours after initiation of the continuous intravenous infusion and for about 12 hours to about 24 hours thereafter.

If desired or medically indicated, amount of ganaxolone infused into the subject by continuous intravenous infusion can be increased, decreased, or remain unchanged per hour starting at about the 24 hours after initiation and for up to 96 hours or longer thereafter. For example, the amount of ganaxolone infused into the subject by continuous intravenous infusion can be decreased to about 30 mg of ganaxolone per hour starting about 24 hours after initiation and for up to 96 hours or longer thereafter.

For example, the amount of ganaxolone infused into the subject by continuous intravenous infusion can be increased up to about 40 mg of ganaxolone per hour starting about 24 hours after initiation and for up to about 96 hours thereafter. In general, the amount of ganaxolone administered to the subject by continuous intravenous infusion does not exceed 40 mg ganaxolone per hour.

Preferably, the amount of ganaxolone administered to the subject does not exceed 1050 mg per day.

In embodiments, about 0.45 to about 0.70 mg/kg of ganaxolone per hour is administered to the subject by continuous intravenous infusion starting about 2 hours after initiation of the continuous intravenous infusion and for about 6 hours to about 10 hours thereafter. Preferably, about 0.57 mg/kg of ganaxolone per hour is administered to the subject by continuous intravenous infusion starting about 2 hours after initiation of the continuous intravenous infusion and for about 6 hours to about 10 hours thereafter. In embodiments, about 0.50 mg/kg of ganaxolone per hour is administered to the subject by continuous intravenous infusion starting about 12 hours after initiation of the continuous intravenous infusion and for up to about 96 hours, about 120 hours, about 144 hours, about 168 hours or longer thereafter.

If desired or medically indicated, the amount of ganaxolone infused into the subject by continuous intravenous infusion can be decreased or increased per hour starting about 24 hours after initiation and for up to about 96 hours, about 120 hours, about 144 hours, about 168 hours or longer thereafter.

The amount of ganaxolone administered to the subject per hour by continuous intravenous infusion can be decreased or increased by increasing or decreasing the rate of infusion. The rate of infusion will generally vary between about 5 mg/hour of ganaxolone to about 130 mg/hour of ganaxolone, depending on clinical response and safety. In certain embodiments, the rate of administration is from about 5 mg/hour to about 90 mg/hour.

The treatment period of the continuous intravenous infusion can be for a period of at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 31 hours, at least 32 hours, at least 33 hours, at least 34 hours, at least 35 hours, at least 36 hours, at least 37 hours, at least 38 hours, at least 39 hours, at least 40 hours, at least 45 hours, at least 50 hours, at least 55 hours, at least 60 hours, at least 65 hours, at least 70 hours, at least 75 hours, at least 80 hours, at least 90 hours, at least 96 hours, or longer after the initiation of the continuous intravenous infusion. A preferred continuous intravenous infusion period is for a period of about 2 hours to about 96 hours after the initiation of the continuous intravenous infusion. Generally, the continuous intravenous infusion is a period of about 96 hours but can be shorter or longer, such as for about 72 hours, about 48 hours, about 24 hours, about 120 hours, about 144 hours, or about 168 hours. Generally, for subject's weighing less than 40 kg, the continuous intravenous infusion is a period of about 36 hours but can be longer, such as for about 48 hours, about 72 hours, or about 96 hours.

During continuous intravenous infusion of ganaxolone, one or more additional intravenous bolus (e.g. 1, 2, 3, 4, 5, 6, 7, 8, 9, or 10) of ganaxolone can be administered to a subject that shows signs of SE re-lapse or experiences SE re-lapse. Electroencephalogram (EEG) can be used to detect signs of SE re-lapse. Plasma concentration of ganaxolone can alternatively or in combination with EEG be used to detect signs of SE re-lapse or a subject that experiences SE re-lapse. For example, a ganaxolone plasma concentration below 400 ng/ml can suggest that the subject is likely to re-lapse.

During continuous intravenous infusion of ganaxolone, 1, 2, 3, 4, 5, 6, 7, 8, 9 or 10 intravenous boluses of ganaxolone can be administered to a subject that shows signs of SE re-lapse or experiences SE re-lapse.

One or more additional intravenous bolus of ganaxolone from about 1 mg to about 100 mg, from about 1 mg to about 90 mg, about 1 mg to about 80 mg, about 2 mg to about 75 mg, from about 3 mg to about 70 mg, from about 5 mg to about 60 mg, from about 5 mg to about 50 mg, from about 5 mg to about 45 mg, or from about 5 mg to about 35 mg may be administered intravenously over about 1 to about 5 minutes, e.g., in the event there is seizure(s) (i.e., abnormal EEG activity) and/or convulsion(s) relapse.

The additional intravenous bolus of ganaxolone can be infused into the subject at an amount of about 1 mg/hr, about 2 mg/hr, about 3 mg/hr, about 4 mg/hr, about 5 mg/hr, about 6 mg/hr, about 7 mg/hr, about 8 mg/hr, about 9 mg/hr, about 10 mg/hr, about 11 mg/hr, about 12 mg/hr, about 13 mg/hr, about 14 mg/hr, about 15 mg/hr, about 16 mg/hr, about 17 mg/hr, about 18 mg/hr, about 19 mg/hr, about 20 mg/hr, about 21 mg/hr, about 22 mg/hr, about 23 mg/hr, about 24 mg/hr, about 25 mg/hr, about 26 mg/hr, about 27 mg/hr, about 28 mg/hr, about 29 mg/hr, about 30 mg/hr, about 31 mg/hr, about 32 mg/hr, about 33 mg/hr, about 34 mg/hr, about 35 mg/hr, about 36 mg/hr, about 37 mg/hr, about 38 mg/hr, about 39 mg/hr, about 40 mg/hr, about 45 mg/hr, about 50 mg/hr, about 55 mg/hr, about 60 mg/hr, about 65 mg/hr, about 70 mg/hr, about 75 mg/hr, about 80 mg/hr, about 85 mg/hr, about 90 mg/hr, about 95 mg/hr, or about 100 mg/hr of ganaxolone per hour prior to seizure re-lapse or upon detection of seizure re-lapse over a period of about 1 minute to about 5 minutes.

The additional intravenous bolus of ganaxolone can be infused into the subject at any time interval during the treatment period of the continuous intravenous infusion of the bolus. Generally, a single intravenous bolus of ganaxolone can be administered up to 24 hours after the initiation of the continuous intravenous infusion. The prescribing clinician will understand that in some instances, more than one intravenous bolus of ganaxolone may be administered to a subject that shows signs of SE re-lapse or experiences SE re-lapse. Thereafter, up to three intravenous boluses of ganaxolone can be administered in a 24 period. For example, 1, 2, or 3 additional intravenous boluses of ganaxolone can be administered to the subject between 25 hours to 48 hours after the initiation of the continuous intravenous infusion. For example, 1, 2, or 3 additional intravenous boluses of ganaxolone can be administered to the subject between 73 hours to 96 hours after the initiation after the continuous intravenous infusion. Given the severity of the condition, the prescribing clinician more than three intravenous boluses of ganaxolone may be administered to a subject that shows signs of SE re-lapse or experiences SE re-lapse.

D. Taper Period

The method for treating SRSE can further comprise continuing to administer to a subject in need thereof the continuous intravenous infusion for a taper period. The taper period follows the continuous intravenous infusion treatment period. Generally, the taper period immediately follows the continuous intravenous infusion treatment period. Although, in some cases, the taper period can immediately follow the target concentration period. When the continuous intravenous has a treatment period of about 36 hours or longer (i.e., 8 hours, about 72 hours, or about 96 hours), the taper period starts immediately after the treatment period.

During the taper period the amount of ganaxolone administered to the subject per hour is reduced by about 5%, about 10%, about 15%, about 20%, about 25%, about 30%, about 35%, about 40%, about 50% or more about every 1 hour, about 2 hours, about 3 hours, about 4 hours, about 5 hours, about 6 hours, about 7 hours, about 8 hours, about 9 hours, about 10 hours, about 11 hours, or about 12 hours until the subject is weaned off ganaxolone. Although, the taper period can be longer than 12 hours. For example, the taper period can be for about 24 hours, about 48 hours, about 96 hours, about 120 hours, about 144 hours, or longer.

During the taper period the amount of ganaxolone administered to the subject per hour is reduced by about one third about every 1 hour, about 2 hours, about 3 hours, about 4 hours, about 5 hours, about 6 hours, about 7 hours, about 8 hours, about 9 hours, about 10 hours, about 11 hours, or about 12 hours. Preferably, during the taper period the amount of ganaxolone administered to the subject per hour is reduced by about one third about every four hours.

As an alternative, the continuous intravenous infusion can be stopped, and oral ganaxolone (e.g., in an oral capsule, an oral tablet, an oral suspension or an oral solution) can be administered to the subject. Oral ganaxolone can be used in place of the taper period to maintain a ganaxolone serum concentration of about 50 ng/ml to about 500 ng/ml.

In certain embodiments, the methods disclosed herein further comprise, after stopping the continuous intravenous infusion of ganaxolone, orally administering ganaxolone to the subject. The oral daily dose of ganaxolone may be, e.g., from about 200 mg to about 3000 mg, from about 400 mg to about 2000 mg, from about 600 mg to about 1900 mg, or from about 900 mg to about 1800 mg, and may be administered in an oral capsule, oral suspension or an oral tablet. In certain embodiments, the oral daily dose of ganaxolone may be, e.g., from about 200 mg to about 2000 mg, from about 400 mg to about 1500 mg, from about 400 mg to about 1250 mg, or from about 400 mg to about 1000 mg, and may be administered in an oral capsule, oral suspension or an oral tablet. The oral administration may continue, e.g., for about 7 days, 14 days, 21 days, 28 days or longer.

In certain embodiments, one or more oral doses of ganaxolone are administered before or after the continuous intravenous infusion or intravenous doses of ganaxolone. The oral daily dose of ganaxolone may be, e.g., from about 200 mg to about 3000 mg, from about 400 mg to about 2000 mg, from about 600 mg to about 1900 mg, or from about 900 mg to about 1800 mg, and may be administered in an oral capsule, oral suspension or an oral tablet. In certain embodiments, the oral daily dose of ganaxolone may be, e.g., from about 200 mg to about 2000 mg, from about 400 mg to about 1500 mg, from about 400 mg to about 1250 mg, or from about 400 mg to about 1000 mg, and may be administered in an oral capsule, oral suspension or an oral tablet. The oral administration may continue, e.g., for about 7 days, 14 days, 21 days, 28 days or longer.

Oral ganaxolone can be administered prior to, during or after the taper period. The oral ganaxolone can maintain ganaxolone plasma concentration at least about 50 ng/ml, at least about 75 ng/ml, at least about 100 ng/ml, at least 125 ng/ml, at least about 150 ng/ml, at least about 175 ng/ml, at least about 200 ng/ml, at least about 225 ng/ml, at least about 225 ng/ml, at least about 250 ng/ml, at least about 275 ng/ml, at least about 300 ng/ml, at least about 325 ng/ml, at least about 350 ng/ml, at least about 375 ng/ml, at least about 400 ng/ml, at least about 425 ng/ml, at least about 450 ng/ml, at least about 475 ng/ml, at least about 500 ng/ml, or 600 ng/ml or higher. It is preferably that the ganaxolone plasma concentration is maintained from at least about 200 ng/ml to about 500 ng/ml.

Oral ganaxolone can be continued after the taper period. Oral ganaxolone may be administered in an oral capsule, oral suspension, or an oral tablet form. Oral ganaxolone may continue, e.g., for about 7 days, 14 days, 21 days, 28 days, 3 months, 6 months, 12 months, or 18 months, or longer. The oral ganaxolone after the taper period can maintain ganaxolone plasma concentration at least about 50 ng/ml, at least about 75 ng/ml, at least about 100 ng/ml, at least 125 ng/ml, at least about 150 ng/ml, at least about 175 ng/ml, at least about 200 ng/ml, at least about 225 ng/ml, at least about 225 ng/ml, at least about 250 ng/ml, at least about 275 ng/ml, at least about 300 ng/ml, at least about 325 ng/ml, at least about 350 ng/ml, at least about 375 ng/ml, at least about 400 ng/ml, at least about 425 ng/ml, at least about 450 ng/ml, at least about 475 ng/ml, at least about 500 ng/ml, or 600 ng/ml or higher. It is preferably that the ganaxolone plasma concentration is maintained from at least about 200 ng/ml to about 500 ng/ml.

Without being bound by theory, administration of oral ganaxolone after the taper period maintains the ganaxolone plasma concentration at least about 50 ng/ml to about 500 ng/ml maintains continued suppression of SE and prevents SE re-lapse.

E. Ganaxolone

Ganaxolone (alternatively known as 3α-hydroxy-3β-methyl-5α-pregnan-20-one, SPT3162, MD 9150000, CCD-1042, Mepalon, and 1042) is the subject of Investigational New Drug Application (IND) No. 129,433. The molecular formula of ganaxolone is $C_{22}H_{36}O_2$, and the chemical structure is:

A

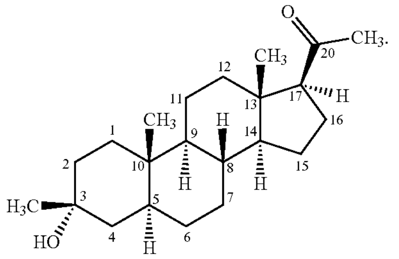

Ganaxolone

Ganaxolone (3α-hydroxy-3β-methyl-5α-pregnan-20-one) is a 3ß-methylated synthetic analogue of the endogenous neurosteroid allopregnanolone with similar biological activity (Carter et al., (1997), The Journal of Pharmacology and Experimental Therapeutics, 280:1284-1295), but it is designed to not activate nuclear (classical) progesterone receptors. Also, in contrast to allopregnanolone, ganaxolone is orally bioavailable.

Ganaxolone acts as a positive allosteric modulator of γ-aminobutyric acid type A ($GABA_A$) receptors in the CNS (Carter et al 1997). Ganaxolone affects $GABA_A$ receptors by interacting with a recognition site that is distinct from other allosteric $GABA_A$ receptor modulators, such as benzodiazepines and barbiturates. Ganaxolone binds to synaptic- and extrasynaptic receptors, mediating both phasic and tonic modulation, respectively. The unique binding of ganaxolone to these two distinct receptor types does not lead to the tolerance seen with benzodiazepines (Mares and Stehlikova (2010) Neurosci. Let. 469:396-399) and allows ganaxolone to act as a broad-spectrum GABAergic compound with the potential to treat the myriad of symptoms related to pediatric genetic epilepsies, refractory seizures, cognitive and behavioral disorders, and sleep dysfunction.

Ganaxolone provides an alternative mechanism in the treatment of seizures and could serve as effective therapy in the management of SE, including generalized convulsive status epilepticus, non-convulsive status epilepticus, early status epilepticus, established status epilepticus, refractory status epilepticus, or super-refractory status epilepticus.

Ganaxolone does not activate the progesterone receptor directly or indirectly, via metabolic conversion, confirming ganaxolone's lack of hormonal activity.

Ganaxolone has the advantage of controlling both convulsive and non-convulsive seizures. In experimental animals, Ganaxolone produced immediate and prolonged cessation of benzodiazepine-resistant SE as evidenced by a block of convulsions, reduction of EEG seizure activity, and increased survival.

Ganaxolone is insoluble in water. Its solubility in 95% alcohol, propylene glycol and polyethylene glycol are 13 mg/mL, 3.5 mg/mL, and 3.1 mg/mL, respectively. Ganaxolone has a relatively long half-life-approximately 20 hours in human plasma following oral administration (Nohria, V. and Giller, E., *Neurotherapeutics,* (2007) 4 (1): 102-105). Furthermore, ganaxolone has a short $T_{max}$, which means that therapeutic blood levels are reached quickly.

Ganaxolone is metabolized by CYP3A4/5, and in vitro data and human PK data from subjects taking strong CYP inducers (carbamazepine and phenytoin) has shown increased ganaxolone clearance with approximately a 45% lowering in overall ganaxolone levels and exposure.

In the ganaxolone development program overall, no clinically significant trends in electrocardiogram (ECG) intervals, vital signs, or physical or neurological examinations have been noted, and no mean changes from baseline in clinical laboratory results have been identified. In the completed placebo-controlled Phase 1, 2, and 3 studies, 0.32% of subjects who received ganaxolone and 0.46% of subjects who received placebo developed elevated LFTs during the study (>3×ULN AST and/or ALT). A subject participating in the ganaxolone paediatric epilepsy study developed liver failure, which was not considered to be related to ganaxolone. The subject was diagnosed with short bowel syndrome, liver steatosis and IgG-cholangitis, which were considered to be the causal factors for the subject's liver failure. There have been no other cases of Hy's Law or liver failure in the ganaxolone development program. It is known that ganaxolone and its metabolites are excreted to breast milk. After cessation of the dosing, plasma ganaxolone levels are expected to drop rapidly, but it is possible that low sub-therapeutic levels persist for several days as ganaxolone is slowly released from tissues.

Previous toxicology studies in animals focusing on pre-natal and neonatal development have not demonstrated toxicities associated with ganaxolone. Ganaxolone has been administered to infants with severe forms of epilepsy as early as 4 months of age. In clinical trials involving administration of ganaxolone over several weeks, the study drug has been tapered off over a 1 to 2-week period. There have been no reports of withdrawal symptoms emerging after cessation of ganaxolone.

F. Formulations

Contemplated herein are formulations that comprise a therapeutically effective amount of a neurosteroid for treating status epilepticus according the methods disclosed herein. Preferably the neurosteroid is ganaxolone. Other neurosteroid that can be used according to the methods disclosed herein include, but are not limited to allopregnanolone, 3α-Dihydroprogesterone, 5α-Dihydroprogesterone, 5ß-Dihydroprogesterone, Allopregnanediol, Dihydrodeoxycorticosterone, Pregnanediol, Pregnanolone, Tetrahydrodeoxycorticosterone, Alfadolone, Alfadolone acetate, EIDD-036, Hydroxydione, Minaxolone, 21-chloro-2β-morpholin-4-yl-5ß-pregnan-3α-ol-20-one, 2β-(2,2-dimethyl-4-morpholinyl)-3α-hydroxy-11,20-dioxo-5α-pregnan-21-yl methanesulfonate, or Renanolone, SGE-516, SGE-872, SAGE-217 (Zuranolone: 3α-hydroxy-3β-methyl-21-(4-cyano-1H-pyrazol-1'-yl)-19-nor-5ß-pregnan-20-one).

The formulation is preferably an intravenous formulation of ganaxolone. The intravenous formulation of ganaxolone can comprise a cyclodextrin (e.g., a sulfobutyl ether β-cyclodextrin (Captisol®). The IV solution can comprise a sterile ready to administer solution containing 1 mg/ml ganaxolone in Captisol® (Captisol®: GNX ratio 60:1). The ready to administer solution can comprise 1 mg/ml ganaxolone in sulfobutyl ether β-cyclodextrin (Captisol®) having a Captisol to ganaxolone ratio of 60:1, and a buffer (i.e., phosphate and/or sodium chloride). In embodiments, the IV solution is a sterile solution containing 3 mg/ml ganaxolone in Captisol® (Sulfobutylether-β-Cyclodextrin) (Captisol®: GNX ratio 70:1) or 5 mg/ml ganaxolone in Captisol, each of which may or may not be may be diluted with 0.9% saline (i.e., sodium chloride) solution, for example to produce a 1 mg/ml ganaxolone solution for administration, prior to administration.

In certain embodiments, the formulation (e.g., an intravenous formulation) comprises ganaxolone and sulfobutylether-β-cyclodextrin (e.g., Captisol®) in a weight ratio from about 1:50 to about 1:75. In some of these embodiments, the weight ratio ganaxolone and Captisol® is about 1:51, about 1:52, about 1:53, about 54:1, about 1:55, about 1:56, about 1:57, about 1:58, about 1:59, about 1:60, about 1:61, about 1:62, about 1:63, about 1:64, about 1:65, about 1:66, about 1:67, about 1:68, about 1:69, about 1:70, about 1:71, or about 1:72. In some of these embodiments, the weight ratio ganaxolone and Captisol® is about 1:60.

The intravenous formulation may be selected, e.g., from the group consisting of nanocrystal formulations; emulsions; lyocells; solvents or surfactants; liposomes; microemulsions; and liquids containing solid-lipid nanoparticles.

In certain embodiments, the intravenous formulation is an IV solution. An intravenous formulation is preferably a sterile liquid (e.g., aqueous liquid in the form of an emulsion, a suspension, a solution and the likes). In some of these embodiments, the IV solution comprises ganaxolone and a pharmaceutically acceptable solvent(s) and/or oil(s) that can solubilize ganaxolone.

In certain embodiments, the intravenous formulation is an oil-in-water emulsion.

In certain embodiments, the intravenous formulation is a liquid nanoparticulate formulation (e.g., a liquid comprising nanoparticles of ganaxolone). In some of the embodiments, the nanoparticulate formulation comprises ganaxolone and a polymeric and/or ionic stabilizer, and is free from complexing agents. In certain embodiments, the polymeric and ionic stabilizers are selected from the group consisting of surfactants. In certain embodiments, surfactants are selected from the group consisting of sorbitan esters, polyoxyethylene sorbitan fatty acid esters, poloxamers, cholesterol salts, and bile salts.

In certain embodiments, the formulation for the intravenous infusion may be a formulation as described and prepared in U.S. Patent Publication No. 2017/0258812 or U.S. Patent Publication No. 2016/0228454. However, formulations for the intravenous infusion may be prepared in accordance with other methods known to those skilled in the art.

As described in U.S. Patent Publication No. 2016/0228454, an aqueous injectable ganaxolone formulation may comprise a) ganaxolone and sulfobutyl ether-β-cyclodextrin in an inclusion complex; and b) water. In some embodiments, the complex comprising ganaxolone and sulfobutyl ether-β-cyclodextrin comprises a 1:1 ganaxolone: sulfobutyl ether-β-cyclodextrin complex; and the w/w ratio of sulfobutyl ether-β-cyclodextrin to ganaxolone is about 52:1 or greater. In some embodiments, the formulation may further comprise surfactant. In some embodiments, the surfactant is a sorbitan ester, a polyoxyethylene sorbitan fatty acid ester, a poloxamer, a cholesterol salt, or a bile salt. In some embodiments, the surfactant may comprise from about 1 to about 15 percent of the formulation by weight. In some embodiments, the surfactant is polysorbate 80. In some embodiments, the formulation further comprises a buffer and has a pH of about 6.0 to about 7.6. In some embodiments, the buffer is a phosphate buffer. In some embodiments, the buffer is a combination of a monobasic phosphate buffer and a dibasic phosphate buffer, wherein the concentration of each phosphate buffer is 2 mM to 50 mM. In some embodiments, the buffer is a phosphate buffer. In some embodiments, the buffer is a combination of a monobasic phosphate buffer and a dibasic phosphate buffer, wherein the concentration of each phosphate buffer is 2 mM to 50 mM. In some embodiments, the concentration of ganaxolone is 2 mg/ml to 8 mg/ml, the w/w ratio of sulfobutyl ether-β-cyclodextrin to ganaxolone is within the range from about 52:1 to about 90:1; the formulation contains a buffer and has a pH of 6.7 to 7.3 or a pH of 6.0 to 7.0; and the formulation contains from 1 to 15 weight percent surfactant. In some embodiments, the concentration of ganaxolone is 1 mg/ml to 5 mg/ml; the weight percent of sulfobutyl ether-β-cyclodextrin 25% to 35%; and the formulation contains from 5% to 15% (weight percent) of at least one of the following: a surfactant, ethanol, glycerin, or propylene glycol. In some embodiments, the formulation further comprises a preservative. In some embodiments, the preservative is benzyl alcohol, chlorbutanol, 2-ethoxyethanol, parabens (including methyl, ethyl, propyl, butyl, and combinations), benzoic acid, sorbic acid, chlorhexidene, phenol, 3-cresol, thimerosal, or a phenylmercurate salt.

As further described in U.S. Patent Publication No. 2016/0228454, the formulation may be a lyophilized ganaxolone formulation comprising ganaxolone and sulfobutyl ether-β-cyclodextrin, wherein the ganaxolone formulation is 1.0% to 1.5% ganaxolone. In some embodiments, the formulation may further comprise a bulking agent. In some embodiments, the bulking agent is mannitol, lactose, sucrose, trehalose, sorbitol, glucose, rafinose, glycine, histidine, polyethylene glycol (PEG), or polyvinyl pyrrolidone (PVP).

Ganaxolone formulations suitable for parenteral administration in the methods of the present invention may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propylene glycol, polyethylene-glycol, glycerol, cremophor and the like), suitable mixtures thereof, vegetable oils (such as olive oil) and injectable organic esters such as ethyl oleate. Additionally, ganaxolone can be dissolved at concentrations of >1 mg/ml using water soluble beta cyclodextrins (e.g. beta-sulfobutyl-cyclodextrin and 2-hydroxypropylbetacyclodextrin). A particularly suitable cyclodextrin is a substituted-β-cyclodextrin is Captisol®. Proper fluidity can be maintained, for example, by the use of a coating such as lecithin, by the maintenance of the required particle size in the case of dispersions, and by the use of surfactants. Ganaxolone formulations suitable for subcutaneous injection may also contain additives such as preserving, wetting, emulsifying, and dispensing agents. Prevention of the growth of microorganisms can be ensured by various antibacterial and antifungal agents, such as parabens, benzoic acid, benzyl alcohol, chlorobutanol, phenol, sorbic acid, and the like. It may also be desirable to include isotonic agents, such as sugars, sodium chloride, and the like. Prolonged drug absorption of the injectable pharmaceutical form can be brought about by the use of agents delaying absorption, such as aluminum monostearate and gelatin. Ganaxolone suspension formulations designed for extended release via subcutaneous or intramuscular injection can avoid first pass metabolism and lower dosages of ganaxolone will be necessary to maintain plasma levels of about 50 ng/ml. In such formulations, the particle size of the ganaxolone particles and the range of the particle sizes of the ganaxolone particles can be used to control the release of the drug by controlling the rate of dissolution in fat or muscle.

In certain embodiments, the intravenous formulation is a solution comprising a complexing agent(s). In some of these embodiments, a complexing agent is a molecule with a lipophilic core and hydrophilic outer shell capable of solubilizing ganaxolone In certain embodiments, the formulation is an IV solution comprising ganaxolone and sulfobutylether cyclodextrin (Captisol®), wherein ganaxolone is solubilized in sulfobutylether cyclodextrin (Captisol®). In some embodiments, the solution comprises 3 mg of ganaxolone per 1 ml of the solution and is sterile. In certain embodiments, the solution is stable for at least 18 months, is stored refrigerated at a temperature from about 4° C. to about 8° C.

In certain embodiments, the liquid formulation of the present invention may be a formulation as described and prepared in U.S. Pat. No. 8,022,054, entitled "Liquid Ganaxolone Formulations and Methods for the Making and Use Thereof", hereby incorporated by reference in its entirety. However, the oral liquid (e.g., suspension) formulation of ganaxolone may be prepared in accordance with other methods known to those skilled in the art.

As described in U.S. Pat. No. 8,022,054, the liquid formulation may be an aqueous dispersion of stabilized particles comprising ganaxolone, a hydrophilic polymer, a wetting agent, and an effective amount of a complexing agent that stabilizes particle growth after an initial particle growth and endpoint is reached, the complexing agent selected from the group of small organic molecules having a molecular weight less than 550 and containing a moiety selected from the group consisting of a phenol moiety, an aromatic ester moiety and an aromatic acid moiety, wherein the stabilized particles have a volume weighted median diameter (D50) of the particles from about 50 nm to about 500 nm, the complexing agent being present in an amount from about 0.05% to about 5%, w/w based on the weight of particles, the particles dispersed in an aqueous solution which further contains at least two preservatives in an amount sufficient to inhibit microbial growth. The hydrophilic polymer may be in an amount from about 3% to about 50%, w/w, based on the weight of the solid particles. The wetting agent may be an amount from about 0.01% to about 10%, w/w, based on the weight of the solid particles. Ganaxolone may be in an amount from about 10% to about 80% (and in certain embodiments form about 50% to about 80%) based on the weight of the stabilized particles. The stabilized particles may exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour as compared to the D50 of the stabilized particles when the particles are dispersed in distilled water under the same conditions, wherein the volume weighted median diameter (D50) of the stabilized particles dispersed in SGF or SIF is less than about 750 nm. The stabilized particles may exhibit an increase in volume weighted median diameter (D50) of not more than about 150% when the formulation is dispersed in 15 mL of SGF or SIF at a concentration of 0.5 to 1 mg ganaxolone/mL as compared to the D50 of the stabilized particles when the particles are dispersed in distilled water under the same conditions, wherein the volume weighted median diameter (D50) of the stabilized particles dispersed in SGF or SIF is less than about 750 nm.

The complexing agent can be any molecule with a lipophilic core and hydrophilic outer shell capable of solubilizing ganaxolone. In certain embodiments, complexing agent can be a substance containing a phenol moiety, an aromatic ester moiety or an aromatic acid moiety. In certain embodiments, complexing agents are selected from the group consisting of parabens, organic acids, carboxylic acids, aromatic acids, aromatic esters, acid salts of amino acids, methyl anthranilate, sodium metabisulphite, ascorbic acid and its derivatives, malic acid, isoascorbic acid, citric acid, tartaric acid, sodium sulphite, sodium bisulphate, tocopherol, water- and fat-soluble derivatives of tocopherol, sulphites, bisulphites and hydrogen sulphites, para-aminobenzoic acid and esters, 2,6-di-t-butyl-alpha-dimethylamino-p-cresol, t-butylhydroquinone, di-t-amylhydroquinone, di-t-butylhydroquinone, butylhydroxytoluene (BHT), butylhydroxyanisole (BHA), pyrocatechol, pyrogallol, propyl/gallate, nordihydroguaiaretic acid, phosphoric acids, sorbic and benzoic acids, esters, ascorbyl palmitate, derivatives and isomeric compounds thereof, pharmaceutically acceptable salts thereof, and mixtures thereof. In certain embodiments, the complexing agent is selected from the group consisting of a paraben, benzoic acid, phenol, sodium benzoate, methyl anthranilate, and the like. The hydrophilic polymer may be a cellulosic polymer, a vinyl polymer and mixtures thereof. The cellulosic polymer may be a cellulose ether, e.g., hydroxypropymethylcellulose. The vinyl polymer may be polyvinyl alcohol, e.g., vinyl pyrrolidone/vinyl acetate copolymer (S630). The wetting agent may be sodium lauryl sulfate, a pharmaceutically acceptable salt of docusate, and mixtures thereof. The aqueous dispersion may further comprise a sweetener, e.g., sucralose. In certain embodiments, the preservative is selected from the group consisting of potassium sorbate, methylparaben, propylparaben, benzoic acid, butylparaben, ethyl alcohol, benzyl alcohol, phenol, benzalkonium chloride, and mixtures of any of the foregoing.

In some embodiments, liquid ganaxolone formulations are provided comprising the ganaxolone particles described herein and at least one dispersing agent or suspending agent for oral administration to a subject. The ganaxolone formulation may be a powder and/or granules for suspension, and upon admixture with water, a substantially uniform suspension is obtained. As described herein, the aqueous dispersion can comprise amorphous and non-amorphous ganaxolone particles of consisting of multiple effective particle sizes such that ganaxolone particles having a smaller effective particle size are absorbed more quickly and ganaxolone particles having a larger effective particle size are absorbed more slowly. In certain embodiments, the aqueous dispersion or suspension is an immediate release formulation. In another embodiment, an aqueous dispersion comprising amorphous ganaxolone particles is formulated such that about 50% of the ganaxolone particles are absorbed within about 3 hours after administration and about 90% of the ganaxolone particles are absorbed within about 10 hours after administration. In other embodiments, addition of a complexing agent to the aqueous dispersion results in a larger span of ganaxolone containing particles to extend the drug absorption phase such that 50-80% of the particles are absorbed in the first 3 hours and about 90% are absorbed by about 10 hours.

A suspension is "substantially uniform" when it is mostly homogenous, that is, when the suspension is composed of approximately the same concentration of ganaxolone at any point throughout the suspension. Preferred embodiments are those that provide concentrations essentially the same (within 15%) when measured at various points in a ganaxolone aqueous oral formulation after shaking. Especially preferred are aqueous suspensions and dispersions, which maintain homogeneity (up to 15% variation) when measured 2 hours after shaking. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

In some embodiments, ganaxolone formulations are powders for aqueous dispersion and comprise stable ganaxolone particles having an effective particle size by weight of less than 500 nm formulated with ganaxolone particles having an effective particle size by weight of greater than 500 nm. In such embodiments, the formulations have a particle size distribution wherein about 10% to about 100% of the ganaxolone particles by weight are between about 75 nm and about 500 nm, about 0% to about 90% of the ganaxolone particles by weight are between about 150 nm and about 400 nm, and about 0% to about 30% of the ganaxolone particles by weight are greater than about 600 nm. The ganaxolone particles describe herein can be amorphous, semi-amorphous, crystalline, semi-crystalline, or mixture thereof.

In one embodiment, the aqueous suspensions or dispersions described herein comprise ganaxolone particles or ganaxolone complex at a concentration of about 20 mg/ml to about 150 mg/ml of suspension. In another embodiment, the aqueous oral dispersions described herein comprise ganaxolone particles or ganaxolone complex particles at a concentration of about 25 mg/ml to about 75 mg/ml of solution. In yet another embodiment, the aqueous oral dispersions described herein comprise ganaxolone particles or ganaxolone complex at a concentration of about 50 mg/ml of suspension. The aqueous dispersions described herein are especially beneficial for the administration of ganaxolone to infants (less than 2 years old), children under 10 years of age and any patient group that is unable to swallow or ingest solid oral dosage forms.

Liquid ganaxolone formulation for oral administration can be aqueous suspensions selected from the group including, but not limited to, pharmaceutically acceptable aqueous oral dispersions, emulsions, solutions, and syrups. See, e.g., Singh et al., Encyclopedia of Pharmaceutical Technology, 2nd Ed., pp. 754-757 (2002). In addition to ganaxolone particles, the liquid dosage forms may comprise additives, such as: (a) disintegrating agents; (b) dispersing agents; (c) wetting agents; (d) at least one preservative, (e) viscosity enhancing agents, (f) at least one sweetening agent, (g) at least one flavoring agent, (h) a complexing agent, and (i) an ionic dispersion modulator. In some embodiments, the aqueous dispersions can further comprise a crystalline inhibitor.

Examples of disintegrating agents for use in the aqueous suspensions and dispersions include, but are not limited to, a starch, e.g., a natural starch such as corn starch or potato starch, a pregelatinized starch such as National 1551 or Amijele®, or sodium starch glycolate such as Promogel® or Explotab®; a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crosspovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropylcellulose ethers (e.g., HPC, HPC-SL, and HPC-L), hydroxypropylmethylcellulose and hydroxypropylmethylcellulose ethers (e.g. HPMC K100, HPMC K4M, HPMC K15M, and HPMC K100M), carboxymethylcellulose sodium, methylcellulose, hydroxyethylcellulose, hydroxypropylmethylcellulose phthalate, hydroxypropylmethylcellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 9080, also known as Poloxamine 9080, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethylcellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908%).

Wetting agents (including surfactants) suitable for the aqueous suspensions and dispersions described herein are known in the art and include, but are not limited to, acetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carpool 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben) and their salts, benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth. In one embodiment, the aqueous liquid dispersion can comprise methylparaben and propylparaben in a concentration ranging from about 0.01% to about 0.3% methylparaben by weight to the weight of the aqueous dispersion and 0.005% to 0.03% propylparaben by weight to the total aqueous dispersion weight. In yet another embodiment, the aqueous liquid dispersion can comprise methylparaben 0.05 to about 0.1 weight % and propylparaben from 0.01-0.02 weight % of the aqueous dispersion.

Suitable viscosity enhancing agents for the aqueous suspensions or dispersions described herein include, but are not limited to, methyl cellulose, xanthan gum, carboxymethylcellulose, hydroxypropyl cellulose, hydroxypropylmethyl cellulose, Plasdone. RTM. S-630, carbomer, polyvinyl alcohol, alginates, acacia, chitosans and combinations thereof. The concentration of the viscosity enhancing agent will depend upon the agent selected and the viscosity desired.

Examples of natural and artificial sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet®. Powder, raspberry, root beer, rum, saccharin, safrole, sorbitol, spearmint, spearmint cream, strawberry, strawberry cream, *stevia*, sucralose, sucrose, sodium saccharin, saccharin, aspartame, acesulfame potassium, mannitol, talin, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof. In one embodiment, the aqueous liquid dispersion can comprise a sweetening agent or flavoring agent in a concentration ranging from about 0.0001% to about 10.0% the weight of the aqueous dispersion. In another embodiment, the aqueous liquid dispersion can comprise a sweetening agent or flavoring agent in a concentration ranging from about 0.0005% to about 5.0% wt % of the aqueous dispersion. In yet another embodiment, the aqueous liquid dispersion can comprise a sweetening agent or flavoring agent in a concentration ranging from about 0.0001% to 0.1 wt %, from about 0.001% to about 0.01 weight %, or from 0.0005% to 0.004% of the aqueous dispersion.

In addition to the additives listed above, the liquid ganaxolone formulations can also comprise inert diluents commonly used in the art, such as water or other solvents, solubilizing agents, and emulsifiers.

In some embodiments, the ganaxolone formulations can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art include, but are not limited to, for example, U.S. Pat. Nos. 5,858,401, 6,667,048, and 6,960, 563.

Exemplary emulsifiers are ethyl alcohol, isopropyl alcohol, ethyl carbonate, ethyl acetate, benzyl alcohol, benzyl benzoate, propylene glycol, 1,3-butyleneglycol, dimethylformamide, sodium lauryl sulfate, sodium docusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In certain preferred embodiments, the liquid pharmaceutical formulation comprising ganaxolone, hydroxypropyl methylcellulose, polyvinyl alcohol, sodium lauryl sulfate, simethicone, methyl paraben, propyl paraben, sodium benzoate, citric acid, and sodium citrate at pH 3.8-4.2. The suspension may comprise ganaxolone at a concentration of 50 mg/ml. The formulation may further comprise a pharmaceutically acceptable sweetener (e.g., sucralose) and/or a pharmaceutically acceptable flavorant (e.g., cherry). The formulation may be enclosed, e.g., in a 120 mL, 180 mL, 240 mL, or 480 ml bottle.

A formulation for oral administration may be an oral solid dosage form (e.g., an oral capsule or tablet) or a liquid (e.g., an oral suspension comprising ganaxolone). In certain embodiments, the oral suspension is administered to the patient via the use of an oral syringe.

In certain embodiments, the liquid formulation of the present invention may be a formulation as described and prepared in Applicant's prior U.S. Pat. No. 8,022,054, entitled "Liquid Ganaxolone Formulations and Methods for the Making and Use Thereof", hereby incorporated by reference in its entirety. However, the oral liquid (e.g., suspension) formulation of ganaxolone may be prepared in accordance with other methods known to those skilled in the art.

In certain preferred embodiments, the oral solid formulation of the present invention may be a formulation as described and prepared in Applicant's prior U.S. Pat. No. 7,858,609, entitled "Solid Ganaxolone Formulations and Methods for the Making and Use Thereof", hereby incorporated by reference in its entirety. However, the oral solid dosage formulation of ganaxolone may be prepared in accordance with other methods known to those skilled in the art.

For example, as disclosed in U.S. Pat. No. 7,858,609, the oral solid formulation may comprise stabilized particles comprising ganaxolone, a hydrophilic polymer, a wetting agent, and an effective amount of a complexing agent that stabilizes particle growth after an initial particle growth and endpoint is reached, the complexing agent being a small organic molecule having a molecular weight less than 550 and containing a moiety selected from the group consisting of a phenol moiety, an aromatic ester moiety and an aromatic acid moiety, wherein the stabilized particles have a volume weighted median diameter (D50) of the particles is from about 50 nm to about 500 nm, the complexing agent being present in an amount from about 0.05% to about 5% w/w, based on the weight particles of the solid. The hydrophilic polymer may be in an amount from about 3% to about 50%, w/w, based on the weight of the solid particles. The wetting agent may be an amount from about 0.01% to about 10%, w/w, based on the weight of the solid particles. Ganaxolone may be in an amount from about 10% to about 80% (and in certain embodiments form about 50% to about 80%) based on the weight of the stabilized particles. The stabilized particles may exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour as compared to the D50 of the stabilized particles when the particles are dispersed in distilled water under the same conditions, wherein the volume weighted median diameter (D50) of the stabilized particles dispersed in SGF or SIF is less than about 750 nm. The stabilized particles may exhibit an increase in volume weighted median diameter (D50) of not more than about 150% when the formulation is dispersed in 15 mL of SGF or SIF at a concentration of 0.5 to 1 mg ganaxolone/mL as compared to the D50 of the stabilized particles when the particles are dispersed in distilled water under the same conditions, wherein the volume weighted median diameter (D50) of the stabilized particles dispersed in SGF or SIF is less than about 750 nm. The solid stabilized particles may be combined with optional excipients and prepared for administration in the form of a powder, or they may be incorporated into a dosage form selected from the group consisting of a tablet or capsule. The complexing agent may be a paraben, benzoic acid, phenol, sodium benzoate, methyl anthranilate, and the like. The hydrophilic polymer may be a cellulosic polymer, a vinyl polymer and mixtures thereof. The cellulosic polymer may be a cellulose ether, e.g., hydroxypropymethylcellulose. The vinyl polymer may be polyvinyl alcohol, e.g., vinyl pyrrolidone/vinyl acetate copolymer (S630). The wetting agent may be sodium lauryl sulfate, a pharmaceutically acceptable salt of docusate, and mixtures thereof. When the particles are incorporated into a solid dosage form, the solid dosage form may further comprise at least one pharmaceutically acceptable excipient, e.g., an ionic dispersion modulator, a water soluble spacer, a disintegrant, a binder, a surfactant, a plasticizer, a lubricant, a diluent and any combinations or mixtures thereof. The water soluble spacer may be a saccharide or an ammonium salt, e.g., fructose, sucrose, glucose, lactose, mannitol. The surfactant may be, e.g., polysorbate. The plasticizer may be, e.g., polyethylene glycol. The disintegrant may be cross-linked sodium carboxymethylcellulose, crospovidone, mixtures thereof, and the like.

A capsule may be prepared, e.g., by placing the bulk blend ganaxolone formulation, described herein, inside of a capsule. In some embodiments, the ganaxolone formulations (non-aqueous suspensions and solutions) are placed in a soft gelatin capsule. In other embodiments, the ganaxolone formulations are placed in standard gelatin capsules or non-gelatin capsules such as capsules comprising HPMC. In other embodiments, the ganaxolone formulations are placed in a sprinkle capsule, wherein the capsule may be swallowed whole or the capsule may be opened and the contents sprinkled on food prior to eating. In some embodiments of the present invention, the therapeutic dose is split into multiple (e.g., two, three, or four) capsules. In some embodiments, the entire dose of the ganaxolone formulation is delivered in a capsule form.

In certain embodiments, each capsule contains either 200 mg or 225 mg ganaxolone, and hydroxypropyl methylcellulose, sucrose, polyethylene glycol 3350, polyethylene glycol 400, sodium lauryl sulfate, sodium benzoate, citric acid anhydrous, sodium methyl paraben, microcrystalline cellulose, 30% Simethicone Emulsion, gelatin capsules, polysorbate 80, and sodium chloride. In some of the embodiments, the size of the capsule is 00.

Alternatively, the oral dosage forms of the present invention may be in the form of a controlled release dosage form, as described in U.S. Pat. No. 7,858,609.

In certain preferred embodiments, the oral solid formulation of the present invention may be a formulation as described and prepared U.S. Pat. No. 8,367,651.

As described in U.S. Pat. No. 8,367,651, solid stabilized particles may comprise ganaxolone, a hydrophilic polymer, a wetting agent, and an effective amount of a complexing agent that stabilizes particle growth after an initial particle growth and endpoint is reached, the complexing agent being a small organic molecule having a molecular weight less than 550 and containing a moiety selected from the group consisting of a phenol moiety, an aromatic ester moiety and an aromatic acid moiety, wherein the stabilized particles have a volume weighted median diameter (D50) of the particles is from about 50 nm to about 500 nm and the concentration of ganaxolone in the solid stabilized particles is at least 50% by weight. The hydrophilic polymer maybe in an amount from about 3% to about 50%, w/w, based on the weight of the solid particles. The wetting agent may be in an amount from about 0.01% to about 10%, w/w, based on the weight of the solid particles. In some of the embodiments, the stabilized particles exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour as compared to the D50 of the stabilized particles when the particles are dispersed in distilled water under the same conditions, wherein the volume weighted median diameter (D50) of the stabilized particles dispersed in SGF or SIF is less than about 750 nm. In some embodiments, the stabilized particles exhibit an increase in volume weighted median diameter (D50) of not more than about 150% when the formulation is dispersed in 15 mL of SGF or SIF at a concentration of 0.5 to 1 mg ganaxolone/mL as compared to the D50 of the stabilized particles when the particles are dispersed in distilled water under the same conditions, wherein the volume weighted median diameter (D50) of the stabilized particles dispersed in SGF or SIF is less than about 750 nm. In some embodiments, ganaxolone may be present in an amount greater than 50% to about 80%, based on the weight of the particles. In some embodiments, the stabilized particles may exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour, as compared to the D50 of the stabilized particles when the particles are dispersed in distilled water under the same conditions, wherein the volume weighted median diameter (D50) of the stabilized particles dispersed in SGF or SIF is less than about 750 nm. In some embodiments, the solid stabilized particles may be in the form of a powder. In some embodiments, the particles may be incorporated into a dosage form selected from the group consisting of a tablet or capsule. In some embodiments, the volume weighted median diameter (D50) of the stabilized particles dispersed in distilled water is from about 100 nm to about 350 nm. In some embodiments, the complexing agent is selected from the group consisting of parabens, benzoic acid, methyl anthranilate, and pharmaceutically acceptable salts thereof and mixtures thereof. In some embodiments, paraben is selected from the group consisting of methylparaben, ethylparaben, propylparaben, pharmaceutically acceptable salts thereof and mixtures thereof. In some embodiments, the hydrophilic polymer is selected from the group consisting of a cellulosic polymer, a vinyl polymer and mixtures thereof. In some embodiments, the cellulosic polymer is a cellulose ether. In some embodiments, the cellulose ether is hydroxypropylmethylcellulose. In some embodiments, the vinyl polymer is polyvinyl alcohol. In some embodiments, the wetting agent is selected from the group consisting of sodium lauryl sulfate, a pharmaceutically acceptable salt of docusate, and mixtures thereof. Is some embodiments, the particles are incorporated into a solid dosage form, further comprising at least one pharmaceutically acceptable excipient selected from the group consisting of an ionic dispersion modulator, an water soluble spacer, a disintegrant, a binder, a surfactant, a plasticizer, a lubricant, and any combinations or mixtures thereof. In some embodiments, the pharmaceutically acceptable excipient comprises an ionic dispersion modulator. In some embodiments, the ionic dispersion modulator is in an amount from about 1% to about 50%, w/w, based on the weight of the solid particles. In some embodiments, the ionic dispersion modulator is a salt. In some embodiments, the ionic dispersion modulator is an inorganic salt is selected from the group consisting of a magnesium salt, a calcium salt, a lithium salt, a potassium salt, a sodium salt and mixtures thereof. In some embodiments, the ionic dispersion modulator is an organic salt is selected from the group consisting of a citrate salt, a succinate salt, a fumarate salt, a malate salt, maleate salt, a tartrate salt, a glutarate salt, a lactate salt and mixtures thereof. In some embodiments, the pharmaceutically acceptable excipient comprises a water soluble spacer. In some embodiments, the water soluble spacer is in an amount from about 2% to about 60%, w/w, based on the weight of the solid particles. In some embodiments, the water soluble spacer is a saccharide or an ammonium salt. In some embodiments, the saccharide is selected from the group consisting of fructose, sucrose, glucose, lactose, mannitol and mixtures thereof. In some embodiments, the disintegrant is selected from the group consisting of cross-linked sodium carboxymethylcellulose, crospovidone and any combinations or mixtures thereof. In some embodiments, the surfactant is a polysorbate. In some embodiments, the plasticizer is polyethylene glycol. In some embodiments, the solid dosage form is an immediate release dosage form. In some embodiments, the solid dosage form is a controlled release dosage form. In some embodiments, the particles are incorporated into an oral solid dosage form comprising (i) a controlled release component comprising a first portion of the stabilized particles; and a controlled release material, and (ii) an immediate release component comprising a second portion of the stabilized particles, the first and second portion of stabilized particles having a volume weighted median diameter (D50) of from about 50 nm to about 500 nm. In some embodiments, the ratio of ganaxolone in controlled release to immediate release is from about 4:1 to about 1:4. In some embodiments, the dosage form provides a therapeutic effect for about 8 to about 24 hours after administration. In some embodiments, the complexing agent is in an amount from about 0.05% to about 5%, w/w, based on the weight of the solid particles. In some embodiments, the complexing agent comprises methylparaben or a salt thereof. In some embodiments, the complexing agent comprises benzoic acid or a salt thereof. In some embodiments, the complexing agent comprises methyl anthranilate. In some embodiments, the formulation includes from about 200 mg to about 800 mg ganaxolone.

As further described in U.S. Pat. No. 8,367,651, solid stabilized particles may also comprise ganaxolone, a hydrophilic polymer, a wetting agent, and an effective amount of a complexing agent selected from the group of small organic molecules having a molecular weight less than 550 and containing a moiety selected from the group consisting of a phenol moiety, an aromatic ester moiety and an aromatic acid moiety, the stabilized particles having a volume weighted median diameter (D50) of the particles from about 50 nm to about 500 nm, the concentration of ganaxolone in the solid stabilized particles being at least 50% by weight. In some embodiments, ganaxolone is present in an amount greater than 50% to about 80%, based on the weight of the particles. In some embodiments, the particles are incorporated into a dosage form selected from the group consisting of a tablet or capsule. In some embodiments, the complexing agent is selected from the group consisting of parabens, benzoic acid, methyl anthranilate, and pharmaceutically acceptable salts thereof and mixtures thereof.

In certain preferred embodiments, the formulation of the present invention may be a pharmaceutical composition described in U.S. Pat. No. 9,029,355.

In certain embodiments, the composition may comprise the ganaxolone nanoparticles as described above, further in formulations as described in U.S. Pat. No. 9,029,355. In some embodiments, the pharmaceutical composition is a compressed tablet. In some embodiments, the pharmaceutical composition is contained inside a capsule.

G. Definitions

Various terms relating to aspects of the description are used throughout the specification and claims. Such terms are to be given their ordinary meaning in the art unless otherwise indicated. Other specifically defined terms are to be construed in a manner consistent with the definitions provided herein.

The term “anesthesia” as used herein refers to the absence of all sensation. For example anesthesia results in amnesia, analgesia, muscle paralysis, and sedation. The abbreviation “EEG” means electroencephalography.

The term “modified Salzburg criteria” as used herein refers EEG criteria for nonconvulsive status epilepticus based on the modified Salzburg criteria which defines status epilepticus as continuous epileptiform discharges of greater than 2.5 Hz, or discharges below 2.5 Hz and associated subtle clinical phenomenon. See, Leitinger et al., Lancet Neurol; 15:1054-1062 (2016).

The terms “subject” and “patient” are used interchangeably herein to refer to any animal, such as any mamma, including but not limited to, humans, non-human primates, rodents, and the like. In some embodiments, the mammal is a mouse. In some embodiments, the mammal is a human.

The term "effective amount" or "therapeutically effective amount" as used herein refers to an amount of a compound described herein (e.g., a neurosteroid such as ganaxolone) that is sufficient to effect the intended result, including, but not limited to disease treatment as illustrated below. The "therapeutically effective amount" can be an amount effective to manage ictal activity (e.g., seizure activity), suppress SRSE, allow the patient to recover from a hyperexcitable state, prevents SE-relapse or can provide continued suppression of SRSE. The therapeutically effective amount can vary depending upon the intended application, or the subject and the disease condition being treated, e.g., the weight and age of the subject, the severity of the disease condition, the manner of administration and the like.

The term "pharmaceutical compositions" as used herein are compositions comprising at least one active agent, such as a compound or salt, solvate, or hydrate of ganaxolone, and at least one other substance, such as a carrier. Pharmaceutical compositions optionally contain one or more additional active agents. When specified, pharmaceutical compositions meet the U.S. FDA's GMP (good manufacturing practice) standards for human or non-human drugs. "Pharmaceutical combinations" are combinations of at least two active agents which may be combined in a single dosage form or provided together in separate dosage forms with instructions that the active agents are to be used together to treat a disorder, such as status epilepticus.

As used herein, the terms "treat," treatment," or "treating" and grammatically related terms, refer to an improvement of any sign, symptoms, or consequence of the disease, such as prolonged survival, less morbidity, and/or a lessening of side effects. As is readily appre

5. EQUIVALENTS

It will be readily apparent to those skilled in the art that other suitable modifications and adaptions of the methods of the invention described herein are obvious and may be made using suitable equivalents without departing from the scope of the disclosure or the embodiments. Having now described certain compounds and methods in detail, the same will be more clearly understood by reference to the following examples, which are introduced for illustration only and not intended to be limiting.

Example 1: Open Label, Expanded Access Protocol to Evaluate the Efficacy and Safety of High Dose Intravenous Ganaxolone in the Treatment of Super Refractory Status Epilepticus An open label study to evaluate the efficacy and safety of intravenous ganaxolone in the treatment of super refractory status epilepticus during the wean of third-line agents will be performed. The primary objective of the study is to determine the response and safety of high dose, 4-day IV ganaxolone infusion to support rapid wean of the third line agents in patients with SRSE who failed benzodiazepines, at least two second-line IV antiepileptic drugs (AEDs), and at least 24 hours of third-line (IV anesthesia) treatment. Secondary objectives of the study include assessing time to SE cessation following ganaxolone administration, identifying the proportion of patients on IV anesthesia for the seizure control at the end of IV ganaxolone infusion, and identifying the proportion of patients requiring IV anesthesia within 30 days of IV ganaxolone initiation.

The success of such wean will be assessed by the investigator based on the clinical and EEG features. The wean will be deemed as successful if EEG pattern is improving, or does not reach 20% ictal burden as defined by the modified Salzburg criteria or patient is clinically improving. Retrospective confirmatory analysis of EEGs will be performed by a central reader.

Prior to initiation of ganaxolone patient's medical condition will be optimized: infections addressed, electrolytes corrected (if not contraindicated please keep K>4.0 and Mg >2.5). Immunotherapies, such as steroids, immunoglobulins, plasma exchange, tocilizumab, siltuximab, anakinra, or rituximab may also be optimized.

The second line AEDs will also be optimized (serum levels in therapeutic ranges, doses maximized) and dosing staggered throughout the 24 hours. When multiple second line AEDs are used, it is encourage that AEDs with different mechanisms of action would be chosen, below is the list of AEDs most often utilized during treatment of SRSE.

TABLE 1

AEDs administered during treatment of SRSE

| Drug | Dose |
|---|---|
| Levetiracetam | 1-4 mg/day |
| Fosphenytoin | 5-7 PE/kg/day |
| Phenytoin | 5-7 mg/kg/day |
| Valproic acid | 15-60 mg/kg/day |
| Phenobarbital | 1-4 mg/kg/day |
| Lacosamide | 200-400 mg/day |
| Topiramate | 400-1600 mg/day |
| Clobazam | 20-40 mg/day |
| Perampanel | 8-12 mg/day |

Before ganaxolone initiation, the third line agents will be weaned rapidly (at least 20% of the dose every 8 hours). If patient is on multiple third line agents, barbiturates will be weaned first, followed by benzodiazepines and eventually propofol. It would be reasonable to continue ketamine throughout the study period.

Ganaxolone will be initiated when the EEG ictal burden of 20% is reached for longer than 30 min as defined by modified Salzburg criteria and no clear clinical improvement is observed. After ganaxolone treatment is initiated, the third-line wean will be accelerated and the patient should be weaned off third-line agents within 48 hours of ganaxolone.

After the ganaxolone treatment has been discontinued, the follow-up period assessments/procedures will be collected every 24 hours for 7 days and then weekly for 4 weeks or discharge from the hospital.

The following ganaxolone dosing schedules are planned: Subjects Weighing at Least 40 kg:

A 30 mg intravenous bolus of ganaxolone (over ~3 minutes) will be administered with a continuous intravenous infusion of 80 mg/hour for 2 hours followed by a continuous intravenous infusion rate of 40 mg/hour for 10 hours, and then 35 mg/hour for the remaining 12 hours of Day 1 (time 0 to 24 hours). The continuous intravenous infusion can be supplemented by a single 30 mg bolus infusion over the first 24 hours. On Day 2, from 25 to 48 hours following ganaxolone initiation, the continuous infusion rate of 40 mg/hour and can be supplemented with 3, 30 mg boluses of ganaxolone as needed per bedside provider. On Day 3, from 49 to 72 hours following ganaxolone initiation, the continuous infusion rate of 40 mg/hour and can be supplemented with 3, 30 mg boluses of ganaxolone as needed per bedside provider. On Day 4, from 73 to 96 hours following ganaxolone initiation, the continuous infusion rate of 40 mg/hour and can be supplemented with 3, 30 mg boluses of ganaxolone as needed per bedside provider. On day 5, 97 to 108 hours following ganaxolone initiation the ganaxolone taper will be initiated. The infusion rate will be reduced by 33.3% every 4 hours until the infusion is stopped 108 hours after ganaxolone initiation.

Subjects Weighing Less than 40 kg:

A 0.43 mg/kg intravenous bolus of ganaxolone (over approximately 3 minutes) will be administered with a continuous intravenous infusion at a dose of 1.14 mg/kg/hour for 2 hours followed by a continuous infusion dose of 0.57 mg/kg/hour for 10 hours, and 0.50 mg/kg/hour for the remaining 12 hours of Day 1 (time 0 to 24 hours). On Day 2, from 25 to 48 hours following ganaxolone initiation, ganaxolone is administered with a continuous intravenous infusion at a dose of 0.57 mg/kg/hr. The continuous intravenous infusion can be supplemented with three 0.43 mg/kg boluses of ganaxolone as needed per bedside provider. On Day 3, from 49 to 72 hours following ganaxolone initiation, the continuous infusion rate will be about 0.57 mg/kg/hour and can be supplemented with three 0.43 mg/kg boluses of ganaxolone as needed per bedside provider. On Day 4, from 73 to 96 hours following ganaxolone initiation, the continuous infusion rate will be about 0.57 mg/kg/hour and can be supplemented with three 0.43 mg/kg boluses of ganaxolone as needed per bedside provider. On day 5, 97 to 108 hours following ganaxolone initiation the ganaxolone taper will be initiated. The infusion rate will be reduced by 33.3% every 4 hours until the infusion is stopped 108 hours after ganaxolone initiation.

Example 2: Case Report 1

A 17-year-old female with a history of sporadic primarily febrile and rare afebrile convulsive seizures in early childhood had been seizure-free for 10 years off medication until she began to have focal seizures with generalization. Seizure semiology was characterized by eye fluttering with rapid bilateral involvement at times with leftward head/eye deviation as clusters prior to generalization. She had recurrent seizures over the first three weeks and was admitted to an outside hospital for SE requiring intubation. Over the course of 7 months at the initial tertiary hospital she had 6 episodes of SE and required intubation 4 times with medically induced coma for seizure suppression. She was transferred to the inpatient pediatric rehabilitation unit after being seizure-free for one month on 5 antiseizure medications (cannabidiol, perampanel, phenobarbital, lacosamide, lorazepam), pyridoxine, ketogenic diet, anakinra, and menstrual suppression.

A thorough infectious, metabolic, genetic, vascular and autoimmune evaluation was non-diagnostic. While in the inpatient rehabilitation unit she developed a fever of 41.7° C. and respiratory viral panel was positive for parainfluenza. SE returned requiring transfer to the ICU for midazolam and pentobarbital infusions. Video-electroencephalogram (vEEG) monitoring throughout her course demonstrated multifocal seizure onset. She was seizure-free for two days after drips were weaned before seizures returned prompting vagus nerve stimulator placement and a prolonged 2-week course of IV pentobarbital titrated to EEG burst suppression. As pentobarbital was weaned off, convulsive seizures returned.

She was granted E-IND approval for a trial of IV to enteric GNX. GNX was administered using an IV bolus followed by infusion over 4 days (with boluses as needed for breakthrough seizures): on day 1 pentobarbital was discontinued; by day 3 clinical and electrographic seizures stopped. On Day 5 she was transitioned from IV to enteric GNX and has remained seizure-free.

One month after ganaxolone initiation, the patient was transferred to inpatient rehabilitation services and she was discharged home 1 month later. She was weaned off the ketogenic diet, anakinra, and felbamate with minimal breakthrough clinical seizures (only in setting of intercurrent illness or decreasing ASMs). More than one year later, the patient's response to ganaxolone and seizure cessation were sustained. Patient continues to be on ganaxolone and 4 other ASMs (valproic acid, brivaracetam, lorazepam, perampanel). See, FIGS. 1, 2, and 3A-3C.

Example 3: Case Report 2

A 4 year old (27 kg) girl with Angelman and Lennox-Gastaut Syndromes presented with refractory tonic (>100/day) and atypical absence seizures with an continuous video EEG showing 2.5 hz continuous slow-spike and wave activity and super refractory status epilepticus. Valproic serum levels were 106 μg/ml, with clobazam 1 mg/kg/d. No response was seen to 1 mg/kg rectal diazepam, IV lorazepam (0.5 mg/kg), ethoxsuccimide 40 mg/kg, perampamil (16 mg×2 doses), or midazolam 2 mg IV. Pentobarbitol anesthetic coma was titrated to 5 mg/kg/hr to maintain burst suppression on EEG. Ethoxsuccimide and perampamil were stopped, and ACTH 150 mg/m2 tried for 3 days without improvement or ability to wean pentobarbitol. Pentobarbitol was rapidly tapered down after 4.5 days 1.5 hours before starting IV GNX obtained by emergency IND. EEG again showed status pattern as at baseline before IV GNX bolus of 0.64 mg/kg over 5 minutes followed by 1.12 mg/kg/hr for two hours, and then maintained at 0.46 mg/kg/hr IV infusion for 5 days followed by rapid taper and starting oral ganaxolone 300 mg/kg TID (second emergent IND). Patient was extubated after 48 hr of IV GNX. She was discharged 5 days later on oral GNX and baseline ASM of valproic acid and clobazam.

Rapid improvement on EEG within 10 minutes of IV GNX was seen, and EEG remained improved overall and resolution of status epilepticus was maintained over the 5 days until weaning IV GNX and converting to oral GNX for discharge 4 days later. Four weeks after discharge the patient who was having 20 seizures per day at baseline was reported to have no clinical seizures after hospitalization of 10 days for SRSE. Patient is mentally and physically returned to her functional baseline.

Example 4: Case Report 3

A 7-year old, previously healthy female presented with encephalopathy and fever and developed super refractory status epilepticus concordant with fever-induced refractory epilepsy syndrome (FIRES). On administration, the patient presented in the emergency department (ED) with fever, abdominal pain, and encephalopathy. Patient was admitted to pediatric intensive care unit (PICU) and placed on video-electroencephalogram (vEEG). See, FIG. 4. A thorough infectious, metabolic, genetic, vascular, and autoimmune evaluation was nondiagnostic.

SE persisted despite multiple ASMs (levetiracetam, valproic acid, perampanel, lacosamide, zonisamide), acetazolamide, ketogenic diet, IV anesthetics midazolam and pentobarbital, and subsequent ketamine infusions. Immunomodulatory therapies with IV methylprednisolone and IVIG were initiated concomitantly.

After multiple ASMs, failed attempts to wean pentobarbital, and ketamine and midazolam infusions, she was treated under EIND approval for a trial of IV-to-enteric ganaxolone. Ganaxolone was administered on hospital day 17 using an IV bolus, followed by infusion over 6 days (with boluses as needed for breakthrough seizures) (FIG. 5). Midazolam was discontinued on day 2 of GNX IV protocol; ketamine was discontinued by day 8 with the assistance of phenobarbital loads and maintenance Anakinra was initiated on day 2 of GNX IV protocol (hospital day 19).

By 4 weeks after admission, patient was more responsive; at 6 weeks, she was transferred from ICU to the floor alert and was responsive with some vocalizations.

Upon admission, MRI demonstrated FLAIR changes in bilateral temporal lobes concerning for prior seizures (FIG. 6A). Subsequent neuroimaging during the acute hospital stay demonstrated evolving changes due to ongoing seizure activity (FIGS. 6B-6C). Her acute hospital course was further complicated by bruxism, movement disorder, vagus nerve stimulator infection, neuropathic pain, and sporadic breakthrough clinical seizures.

At discharge, patient remained on numerous ASMs, including levetiracetam, lacosamide, perampanel, phenobarbital, lorazepam, ganaxolone, anakinra, and tetrabenazine.

By 6 months after discharge, she was weaned off perampanel, anakinra, and tetrabenazine. She continues on levetiracetam, lacosamide, phenobarbital, lorazepam, and ganaxolone in addition to iron and pregabalin and attends school with modification.

The invention claimed is:

1. A method for treating super refractory status epilepticus (SRSE), comprising:

a) rapidly weaning a subject in need thereof off an anesthetic agent;

b) administering to the subject a therapeutically effective amount of ganaxolone in an amount sufficient to suppress unacceptable ictal activity, wherein ganaxolone is administered as an intravenous bolus of ganaxolone and a continuous intravenous infusion of ganaxolone, and wherein ganaxolone is administered for a target concentration period of at least about 2.5 hours up to about 5 days, and produces a ganaxolone plasma concentration in the subject of at least about 800 ng/ml throughout the target concentration period;

c) continuing to administer the continuous intravenous infusion for a taper period, wherein the taper period starts at about 36 hours up to about 96 hours from the initiation of the continuous intravenous infusion; and d) orally administering ganaxolone to the subject for about 7 days or longer after the taper period is stopped, wherein the orally administered ganaxolone maintains a ganaxolone plasma concentration in the subject from at least about 200 ng/ml to about 500 ng/ml.

2. The method of claim 1, wherein the subject is weaned off the anesthetic agent until unacceptable ictal activity returns.

3. The method of claim 1, wherein the intravenous bolus produces a ganaxolone plasma concentration in the subject of at least about 800 ng/ml to about 1200 ng/ml.

4. The method of claim 1, wherein the target concentration period is for at least about 2.5 hours.

5. The method of claim 1, wherein the amount of ganaxolone administered to the subject per hour by continuous intravenous infusion is decreased about 2 hours after the initiation of the continuous intravenous infusion.

6. The method of claim 5, wherein the amount of ganaxolone administered to the subject per hour by continuous intravenous infusion is decreased by about 50%, relative to the amount administered per hour at the initiation of the continuous intravenous infusion, about 2 hours after the initiation of the continuous intravenous infusion.

7. The method of claim 1, wherein the amount of ganaxolone administered to the subject per hour by continuous intravenous infusion is decreased about 10 hours to about 14 hours after the initiation of the continuous intravenous infusion.

8. The method of claim 7, wherein the amount of ganaxolone administered to the subject per hour by continuous intravenous infusion is decreased by about 55%-75%, relative to the amount administered per hour at the initiation of the continuous intravenous infusion, about 10 hours to about 14 hours after the initiation of the continuous intravenous infusion.

9. The method of claim 1, wherein the amount of ganaxolone administered to the subject per hour by continuous intravenous infusion is decreased about 2 hours after the initiation of the continuous intravenous infusion, and then about 10 hours to about 14 hours after the initiation of the continuous intravenous infusion.

10. The method of claim 9, wherein the amount of ganaxolone administered to the subject per hour by continuous intravenous infusion is decreased by about 50%, relative to the amount administered per hour at the initiation of the continuous intravenous infusion, about 2 hours after the initiation of the continuous infusion, and then by about 55%-75%, relative to the amount administered per hour at the initiation of the continuous intravenous infusion, about 10 hours to about 14 hours after the initiation of the continuous infusion.

11. The method of claim 1, wherein the continuous intravenous infusion is administered for a treatment period of about 96 hours after the initiation of the continuous intravenous infusion.

12. The method of claim 1, wherein the continuous intravenous infusion is administered for a period of about 36 hours after the initiation of the continuous intravenous infusion.

13. The method of claim 1, wherein the treatment period of the continuous intravenous infusion is for a period of at least about 2 hours to about 96 hours after the initiation of the continuous intravenous infusion.

14. The method of claim 1, wherein the amount of ganaxolone administered to the subject per hour by continuous intravenous infusion is increased after about 15 hours from the initiation of the continuous intravenous infusion.

15. The method of claim 14, wherein the amount of ganaxolone administered to the subject per hour by continuous intravenous infusion is increased by up to about 45%, relative to the amount administered per hour starting after about 24 hours after initiation of the continuous intravenous infusion.

16. The method of claim 14, wherein the amount of ganaxolone administered to the subject per hour by continuous intravenous infusion is increased for a period up to about 96 hours.

* * * * *